(12) United States Patent
Nukavarapu et al.

(10) Patent No.: US 9,707,322 B2
(45) Date of Patent: Jul. 18, 2017

(54) GRADIENT POROUS SCAFFOLDS

(71) Applicant: University of Connecticut, Farmington, CT (US)

(72) Inventors: Syam P. Nukavarapu, South Windsor, CT (US); Cato T. Laurencin, Avon, CT (US); Ami R. Amini, Farmington, CT (US); Deborah L. Dorcemus, Danbury, CT (US)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 14/136,410

(22) Filed: Dec. 20, 2013

(65) Prior Publication Data
US 2014/0178455 A1    Jun. 26, 2014

Related U.S. Application Data

(60) Provisional application No. 61/740,795, filed on Dec. 21, 2012.

(51) Int. Cl.
| | |
|---|---|
| *A61L 27/58* | (2006.01) |
| *A61L 27/18* | (2006.01) |
| *A61L 27/38* | (2006.01) |
| *A61L 27/48* | (2006.01) |
| *A61L 27/52* | (2006.01) |
| *A61L 27/54* | (2006.01) |
| *A61L 27/56* | (2006.01) |

(52) U.S. Cl.
CPC .............. *A61L 27/58* (2013.01); *A61L 27/18* (2013.01); *A61L 27/38* (2013.01); *A61L 27/48* (2013.01); *A61L 27/52* (2013.01); *A61L 27/54* (2013.01); *A61L 27/56* (2013.01)

(58) Field of Classification Search
CPC .......... A61L 27/18; A61L 27/38; A61L 27/48; A61L 27/52; A61L 27/54; A61L 27/56; A61L 27/58
See application file for complete search history.

(56) References Cited

U.S. PATENT DOCUMENTS

| | | | |
|---|---|---|---|
| 2006/0067969 A1* | 3/2006 | Lu et al. ................ | 424/423 |
| 2010/0249931 A1* | 9/2010 | Laurencin et al. ........ | 623/16.11 |
| 2011/0105305 A1* | 5/2011 | Del-Gallo .......... | B01D 39/2051 502/74 |

OTHER PUBLICATIONS

Laurencin C, Khan Y, El-Amin SF. Bone graft substitutes. Expert Rev Med Devices. 2006;3(1):49-57.
Pneumaticos SG, Triantafyllopoulos GK, Basdra EK, Papavassiliou AG. Segmental bone defects: from cellular and molecular pathways to the development of novel biological treatments. J Cell Mol Med. 2010;14(11):2561-9.
Ma PX, Choi JW. Biodegradable polymer scaffolds with well-defined interconnected spherical pore network. Tissue Eng. 2001;7(1):23-33.
Amini AR, Laurencin CT, Nukavarapu SP. 2012. Bone tissue engineering: recent advances and challenges. Crit Rev Biomed Eng. 40(5):363-408.
Arrington ED, Smith WJ, Chambers HG, Bucknell AL, Davino NA. Complications of iliac crest bone graft harvesting. Clin Orthop Relat Res. 1996(329):300-9.
Lord CF, Gebhardt MC, Tomford WW, Mankin HJ. Infection in bone allografts. Incidence, nature, and treatment. J Bone Joint Surg Am. 1988;70(3):369-76.
Delloye C, Cornu O, Druez V, Barbier O. Bone allografts: What they can offer and what they cannot. J Bone Joint Surg Br. 2007;89(5):574-9.
Nukavarapu S, Wallace J, Elgendy H, Lieberman J, Laurencin C. Bone and Biomaterials. An Introduction to Biomaterials and their Applications. 2nd edn., Taylor & Francis group/CRC Press (2011) pp. 571-593.
Vaccaro AR. The role of the osteoconductive scaffold in synthetic bone graft. Orthopedics. 2002;25(5 Suppl):s571-8.
Karageorgiou V, Kaplan D. Porosity of 3D biomaterial scaffolds and osteogenesis. Biomaterials. 2005;26(27):5474-91.
Kuboki Y, Jin Q, Takita H. Geometry of carriers controlling phenotypic expression in BMP-induced osteogenesis and chondrogenesis. J Bone Joint Surg Am. 2001;83-A Suppl 1(Pt 2):S105-15.
Kühne J, Bartl R, Frisch B, Hammer C, Jansson V, Zimmer M. Bone formation in coralline hydroxyapatite. Effects of pore size studied in rabbits. Acta Orthop Scand. 1994;65(3):246-52.
Holtorf HL, Datta N, Jansen JA, Mikos AG. Scaffold mesh size affects the osteoblastic differentiation of seeded marrow stromal cells cultured in a flow perfusion bioreactor. J Biomed Mater Res A. 2005;74(2):171-80.
Nam YS, Yoon JJ, Park TG. A novel fabrication method of macroporous biodegradable polymer scaffolds using gas foaming salt as a porogen additive. J Biomed Mater Res. 2000;53(1):1-7.
Wei G, Ma PX. Macroporous and nanofibrous polymer scaffolds and polymer/bone-like apatite composite scaffolds generated by sugar spheres. J Biomed Mater Res A. 2006;78(2):306-15.
Teng, et al. "Preparation and Characterization of Porous PDLLA/HA Composite Foams by Supercritical Carbon Dioxide Technology," Journal of Biomedical Materials Research Part B: Applied Biomaterials, 81B: 185-193, 2007.
Borden M, Attawia M, Khan Y, Laurencin C. Tissue engineered microsphere-based matrices for bone repair: design and evaluation. Biomaterials. 2002;23(2):551-9.
Jiang T, Nukavarapu S, Deng M, Jabbarzadeh E, Kofron M, Doty S, et al. Chitosan-poly(lactide-co-glycolide) microsphere-based scaffolds for bone tissue engineering: In vitro degradation and in vivo bone regeneration studies. Acta Biomater. 2010.
Klenke FM, Liu Y, Yuan H, Hunziker EB, Siebenrock KA, Hofstetter W. Impact of pore size on the vascularization and osseointegration of ceramic bone substitutes in vivo. J Biomed Mater Res A. 2008;85(3):777-86.
Yaszemski MJ, Payne RG, Hayes WC, Langer R, Mikos AG. Evolution of bone transplantation: molecular, cellular and tissue strategies to engineer human bone. Biomaterials. 1996;17(2):175-85.

(Continued)

*Primary Examiner* — Kyle Purdy
(74) *Attorney, Agent, or Firm* — McDonnell Boehnen Hulbert & Berghoff LLP

(57) ABSTRACT

The present invention provides gradient porous scaffolds for bone regeneration and osteochondral defect repair, methods for making such gradient porous scaffolds, and methods for using the gradient porous scaffolds.

18 Claims, 23 Drawing Sheets

(56) References Cited

OTHER PUBLICATIONS

Eiselt P, Kim BS, Chacko B, Isenberg B, Peters MC, Greene KG, et al. Development of technologies aiding large-tissue engineering. Biotechnol Prog. 1998;14(1):134-40.

Simmons CA, Alsberg E, Hsiong S, Kim WJ, Mooney DJ. Dual growth factor delivery and controlled scaffold degradation enhance in vivo bone formation by transplanted bone marrow stromal cells. Bone. 2004;35(2):562-9.

Amini, A., D. Adams, C. Laurencin & S. P. Nukavarapu. 2012. Optimally porous and biomechanically compatible scaffolds for large-area bone regeneration. Tissue Eng Part A.18(13-14):1376-88.

Borden, M., M. Attawia & C. T. Laurencin (2002) The sintered microsphere matrix for bone tissue engineering: in vitro osteoconductivity studies. J Biomed Mater Res, 61, 421-9.

Davis, M. E., P. C. Hsieh, T. Takahashi, Q. Song, S. Zhang, R. D. Kamm, A. J. Grodzinsky, P. Anversa & R. T. Lee (2006) Local myocardial insulin-like growth factor 1 (IGF-1) delivery with biotinylated peptide nanofibers improves cell therapy for myocardial infarction. Proc Natl Acad Sci USA, 103, 8155-60.

Hosseinkhani, H., M. Hosseinkhani & H. Kobayashi (2006) Proliferation and differentiation of mesenchymal stem cells using self-assembled peptide amphiphile nanofibers. Biomed Mater, 1, 8-15.

Lee, K., E. A. Silva & D. J. Mooney (2011) Growth factor delivery-based tissue engineering: general approaches and a review of recent developments. J R Soc Interface, 8, 153-70.

Mondrinos, M. J., R. Dembzynski, L. Lu, V. K. Byrapogu, D. M. Wootton, P. I. Lelkes & J. Zhou (2006) Porogen-based solid freeform fabrication of polycaprolactone-calcium phosphate scaffolds for tissue engineering. Biomaterials, 27, 4399-408.

Nakahara, H., H. Misawa, A. Yoshida, T. Hayashi, M. Tanaka, T. Furumatsu, N. Tanaka, N. Kobayashi & T. Ozaki (2010) Bone repair using a hybrid scaffold of self-assembling peptide PuraMatrix and polyetheretherketone cage in rats. Cell Transplant, 19, 791-7.

Sargeant, T. D., M. O. Guler, S. M. Oppenheimer, A. Mata, R. L. Satcher, D. C. Dunand & S. I. Stupp (2008) Hybrid bone implants: self-assembly of peptide amphiphile nanofibers within porous titanium. Biomaterials, 29, 161-71.

Uludag, H., D. D'Augusta, R. Palmer, G. Timony & J. Wozney (1999a) Characterization of rhBMP-2 pharmacokinetics implanted with biomaterial carriers in the rat ectopic model. J Biomed Mater Res, 46, 193-202.

Nukavarapu SP, Dorcemus DL. 2013. Osteochondral tissue engineering: current strategies and challenges. Biotechnol Adv. 31(5):706-21.

Igwe JC, Mikael PE, Nukavarapu SP. 2014. Design, fabrication and in vitro evaluation of a novel polymer-hydrogel hybrid scaffold for bone tissue engineering. J Tissue Eng Regen Med. 8(2):131-42.

Pothirajan P, Dorcemus D, Nukavarapu S, Kotecha M. 2014. True MRI assessment of stem cell chondrogenesis in a tissue engineered matrix. Conf Proc IEEE Eng Med Biol Soc. 2014;2014:3933-6.

Dorcemus D, Nukavarapu SP. 2014. Novel and Unique Matrix Design for Osteochondral Tissue Engineering. MRS Proceedings 1621, 17-23.

\* cited by examiner

Low Pore Size · High Pore Size

Increasing Porosity

US 9,707,322 B2

GRADIENT POROUS SCAFFOLDS

RELATED APPLICATIONS

This application claims priority to U.S. Provisional Patent Application Ser. No. 61/740,795 filed Dec. 21, 2012, incorporated by reference herein in its entirety.

BACKGROUND

Osteochondral defects cover subchondral bone and cartilage regions with a gradual change in the tissue structure from bone to cartilage. Currently available fabricated scaffolds for osteochondral repair have shown limited success due to their failure to mimic the zonal structure of native tissue. Articular cartilage is organized into zonal structure (deep, middle, and superficial zones). The deep zone is close to the bony end and is mechanically stiff, while the middle and superficial zones consist of soft cartilage. There is gradual change in the amount of collagen and proteoglycans present from deep to superficial zones.

SUMMARY OF THE INVENTION

In a first aspect, the present invention provides gradient porous scaffolds, comprising a plurality of biodegradable microspheres that are joined to form a scaffold, wherein the scaffold comprises a porosity gradient along a length of the scaffold. In one embodiment, the microspheres are between about 200 μm in diameter and about 700 μm in diameter. In another embodiment, the biodegradable microspheres comprise poly(lactide-co-glycolide acid) (PLGA). In a further embodiment the scaffold further comprises a gel, such as a hydrogel within the scaffold. In another embodiment, the scaffold further comprises cells and/or growth factors associated with the scaffold.

In a second aspect, the invention provides methods for making a gradient porous scaffold, comprising:
(a) mixing a plurality of microspheres with porogen in a desired ratio to produce a mixture, wherein the mixing comprises,
  (i) mixing the plurality of microspheres with different ratios of porogen to produce a plurality of mixes;
  (ii) combining the plurality of mixes to produce the mixture, such that a ratio of the porogen increases along a length of the mixture;
(b) sintering the mixture for a suitable time and under suitable conditions to bond adjacent microspheres, producing a sintered mixture; and
(c) leaching porogen from the sintered mixture to produce a gradient porous scaffold.

In one embodiment, the microspheres are PLGA microspheres. In another embodiment, the microspheres are between about 200 μm in diameter and about 700 μm in diameter. In a further embodiment, the porogen comprises NaCl. In another embodiment, the porogen is between about 100 μm in diameter and about 400 μm in diameter. In a still further embodiment, the weight (wt) % of porogen with respect to microspheres is between about 1 wt % to about 50 wt %. In another embodiment, the sintering comprises thermal sintering or liquid sintering. In further embodiments, the method further comprises introducing a gel (such as a hydrogel) into the gradient porous scaffold, and/or incorporating cells and/or growth factors into the gradient porous scaffold.

In a third aspect, the invention provides methods for bone regeneration or osteochondral defect repair, comprising transplanting the gradient porous scaffold of any embodiment or combination of embodiments of the invention into a subject in need thereof, so as to effect bone regeneration or osteochondral defect repair in the subject.

DETAILED DESCRIPTION OF THE INVENTION

Figure 1:
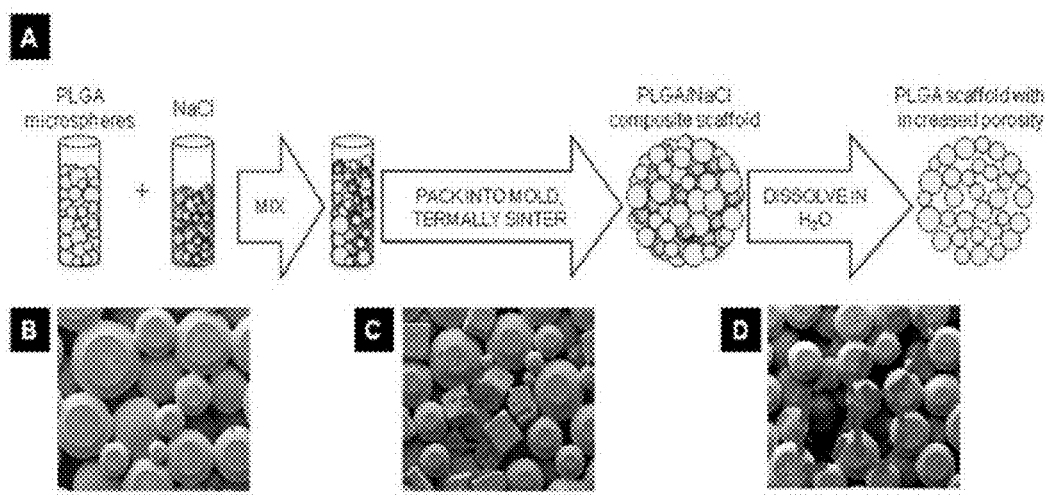
FIG. 1. (A) Schematic diagram illustrating the fabrication process of PLGA microsphere scaffolds with increased porosity. SEM image of (B) PLGA microspheres after thermal sintering, (C) PLGA/NaCl composite scaffold after sintering (arrows indicate NaCl crystals), and (D) PLGA scaffold with increased porosity created after thermal sintering followed by porogen leaching (dotted circles highlight increased pore sizes).

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including", and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The term "about" as used herein means +/−5% of the recited value.

Any terms not directly defined herein shall be understood to have the meanings commonly associated with them as understood within the art of the present disclosure. Certain terms are discussed herein to provide additional guidance to the practitioner in describing the compositions, devices, methods, and the like, of embodiments of the present disclosure, and how to make or use them. It will be appreciated that the same thing can be said in more than one way. Consequently, alternative language and synonyms can be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the embodiments of the present disclosure herein.

All embodiments disclosed herein can be used in combination, unless the context clearly indicates otherwise. When used in this application, the words "herein," "above," and "below," and words of similar import shall refer to the application as a whole and not to any particular portions of the application.

The following description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure. Persons skilled in the relevant art can appreciate that many modifications and variations are possible in light of the embodiment teachings. Accordingly, the disclosure is intended to be illustrative, but not limiting, of the scope of invention.

In a first aspect, the present invention provides gradient porous scaffolds, comprising a plurality of biodegradable microspheres that are joined to form a scaffold, wherein the scaffold comprises a porosity gradient along a length of the scaffold.

Articular cartilage is organized into zonal structure (deep, middle, and superficial zones). The deep zone is close to the bony end and is mechanically stiff, while the middle and superficial zones consist of soft cartilage. There is gradual change in the amount of collagen and proteoglycans present from deep to superficial zones. The scaffolds of the invention mimic the native osteochondral structure physically while supporting chondroprogenitor cell survival, and thus are particularly well suited for use as implants for promoting bone regeneration and osteochondral defect repair.

Figure 20:
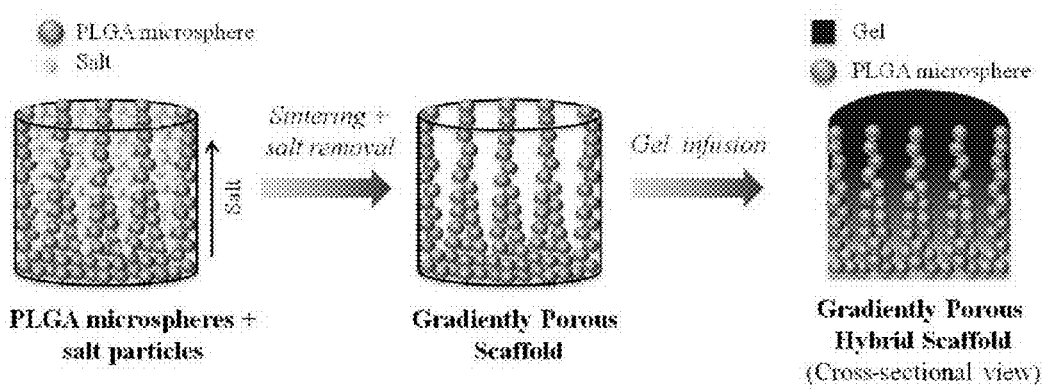
FIG. 20. Schematic showing the method of making grandiently porous hybrid grafts.

As used herein, a "porosity gradient" means that the pore volume of the scaffold increase along the length of the scaffold. For example, in one embodiment the scaffold extends upward with a larger pore volume from bottom to top that mimics the deep to middle zone of the articular cartilage. An exemplary representation of such a gradient porous scaffold is shown in FIG. 20. As used herein, a "length" of the scaffold refers to a length and/or height of the scaffold, as most suitable for an intended use. The porosity gradient may be any suitable gradient as deemed appropriate for an intended use.

In one embodiment, the porosity gradient is designed to mimic human osteochondral tissue or allograft osteochondral plugs. By way of non-limiting example, such an embodiment of the porosity gradient may be structured as follows:

(a) Subchondral bone zone: Starting at a first end of the scaffold and running about 40% to about 70% of the scaffold length, the pore volume ranges between about 10% to about 40%, to mimic subchondral bone. In various other embodiments of this zone, the pore volume ranges between about 10% to about 30%, about 20% to about 40%, or about 20% to about 30%. In various other embodiments, the subchondral bone zone runs about 40% to about 60%. about 40% to about 50%, about 50% to about 70%, about 50% to about 60%, or about 50% of the scaffold length.

(b) Deep zone: Starting contiguous to the subchondral bone zone and running about 5% to about 20% of the scaffold length to mimic the deep zone, the pore volume ranges between about 45% to about 55%. In various other embodiments of this zone, the pore volume ranges between about 45% to about 50%, 50% to about 55%, or is about 45% or 50%. In various other embodiments, the deep zone runs about 5% to about 15%, about 5% to about 10%, about 10% to about 20%, about 10% to about 15%, or about 5%, 10%, 15%, or 20% of the scaffold length.

(c) Middle zone: Starting contiguous to the deep zone and running about 5% to about 20% of the scaffold length to mimic the middle zone, the pore volume ranges between about 55% to about 65%. In various other embodiments of this zone, the pore volume ranges between about 55% to about 60%, 60% to about 65%, or is about 55% or 60%. In various other embodiments, the deep zone runs about 5% to about 15%, about 5% to about 10%, about 10% to about 20%, about 10% to about 15%, or about 5%, 10%, 15%, or 20% of the scaffold length.

(d) Superficial zone: Starting contiguous to the middle zone and running about 5% to about 20% of the scaffold length to mimic the superficial zone, the pore volume ranges between about 65% to about 75%. In various other embodiments of this zone, the pore volume ranges between about 65% to about 70%, 70% to about 75%, or is about 65% or 70%. In various other embodiments, the deep zone runs about 5% to about 15%, about 5% to about 10%, about 10% to about 20%, about 10% to about 15%, or about 5%, 10%, 15%, or 20% of the scaffold length.

The microspheres are spherical particles, with diameters in the micrometer range (i.e. 1 μm to 1000 μm). The diameters may be any that are suitable for an intended use of the scaffold. In one embodiment, the microspheres are 100 μm or greater in diameter (i.e., 100 μm, 150 μm, 200 μm, 250 μm, 300 μm, 350 μm, 400 μm, 450 μm, 500 μm, or greater in diameter. In another embodiment, the microspheres are between about 200 μm in diameter and about 700 μm in diameter.

As will be understood by those of skill in the art, the plurality of microspheres may comprise microspheres of the same/similar diameter, or may comprise microspheres of a variety of diameters. The number of microspheres suitable for a given scaffold can be determined by those of skill in the art based on the teachings herein in light of the size of the scaffold and its intended use.

The microspheres may be of any biodegradable material or combination of biodegradable materials suitable for an intended use. Biodegradable polymers, both natural and synthetic, are known in the art and include, but are not limited to, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, chitin, chitosan, poly(L-lactic acid), poly(lactide-co-glycolide), poly(hydroxybutyrate-co-valerate), and copolymers, terpolymers, or combinations or mixtures of the above materials. Suitable biodegradable polymers can be chosen by the person skilled in the art using standard techniques and based on the mechanical and degradation properties of the polymer such that the polymer is chosen for its compatibility with bone regeneration. In one embodiment, the biodegradable polymer comprises, consists essentially of, or consists of poly (lactic acid-glycolic acid) (also referred to as poly(lactic-co-glycolic acid) or poly(lactide-co-glycolide acid) (PLGA). In one embodiment, the PLGA is 85:15 PLGA (referring to the molar ratio of lactic acid to glycolic acid). In another embodiment, the PLGA is 50:50 PLGA, 65:35 PLGA, and the like.

The microspheres are "joined," in that the microspheres share surface area. The microspheres can be joined via any suitable method, including but not limited to sintering, such as thermal or chemical sintering.

The resulting scaffold may be of any suitable size or shape for an intended purpose. As will be understood by those of skill in the art, any size or shape scaffold can be made by using an appropriate mold. In one non-limiting embodiment, the scaffold comprises a cylindrical shape. In a further non-limiting embodiment, scaffolds between about 3 mm×3 mm and about 50 mm×15 mm (diameter×height) can be made. In various further non-limiting embodiments, the scaffolds may be between about 3×3 mm and about 40×15 mm; about 4×4 mm and about 50×15 mm; about 5×5 mm and about 50×15 mm; about 5×10 mm and about 50×15 mm; about 4×8 mm and about 50×15 mm; about 5×10 mm and about 40×15 mm; about 4×8 mm and about 40×15 mm; about 5×10 mm and about 30×15 mm; about 4×8 mm and about 30×15 mm; about 5×10 mm and about 30×10 mm; about 4×8 mm and about 30×10 mm; about 3 mm×3 mm; about 50 mm×15 mm; about 5 mm×10 mm; or about 4 mm×8 mm.

In another embodiment, the gradient porous scaffolds further comprise a gel hydrogel within the scaffold. In this embodiment, the scaffold comprises a gel within the interior of the scaffold; the scaffold may further comprise a gel on all or a portion of the scaffold surface. As used herein a "gel" is a dilute cross-linked system, which exhibits no flow when in the steady-state. Any suitable material can be used that readily forms into a gel after introduction into the scaffold, or is a gel at the time of introduction into the scaffold. Exemplary such gels include, but are not limited to gelatin, cellulose, or bovine collagen, or a biodegradable synthetic adhesive such as poly ethylene glycol (PEG). In another embodiment, the gel comprises a hydrogel. "Hydrogel" refers to a substance formed when an organic polymer (natural or synthetic) is crosslinked via covalent, ionic, or hydrogen bonds to create a three-dimensional open-lattice structure which entraps water molecules to form a gel. Exemplary hydrogels that can be used in the scaffolds of the invention include, but are not limited to acrylic acid polymers and copolymers, polysaccharides such as alginate, polyphosphazines, poly(acrylic acids), poly(methacrylic acids), poly(alkylene oxides), poly(vinyl acetate), polyvinylpyrrolidone (PVP), glycosaminoglycans (such as chondroitin sulphate, dermatan sulphate, keratan sulphate, heparin or heparan sulphate), hyaluronic acid, polypeptide polymers, including but not limited to self-assembling peptides as disclosed in the examples that follow, and blends and co-polymers thereof. This "hybrid" scaffold design is such that initially the hydrogel can house cells and provide an extracellular matrix-like environment, but slowly as the hydrogel phase starts degrading the cells migrate towards the microsphere surfaces. Thus, the hydrogel can act as a cell encapsulating agent and also provide the nano-topography necessary for the cells to attach and proliferate after scaffold implantation. Furthermore, the hybrid scaffold system promoted increased pre-osteoblastic cell proliferation.

In another embodiment, the scaffold further comprises cells and/or growth factors associated with the scaffold. This embodiment further enhances the use of the scaffolds of the invention for use in promoting bone regeneration and osteochondral defect repair. The cells and growth factors may promote proliferation and/or differentiation of cells of interest. Growth factors may be attached to the microspheres, or may be linked to or encapsulated in the hydrogel when present. Any suitable method for linking growth factors to the scaffold and/or hydrogel may be used. Similarly, the cells may be housed with the hydrogel when present in the scaffold. Since the gradient scaffold can be cellularized by infiltrating with a hydrogel containing cells, intra-operative tissue engineering can be practiced. Any suitable cells and growth factors can be used as appropriate for an intended use of the scaffolds. In one embodiment, the cells may comprise stem cells, osteoblasts, chondrocytes, precursors thereof, and combinations thereof.

In another embodiment, the growth factors may comprise bone morphogenetic protein (BMP) (including but not limited to BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; and BMP-18), Cbfa 1, insulin-like growth factors, interleukin-1, interleukin-6, tumor necrosis factor, Wnt5a, fibroblast growth factor (FGF) (such as FGF2), transforming growth factors (TGFs) (including TGF-$\beta$1, TGF-$\beta$2, and TGF-$\beta$3), Vascular endothelial growth factors (VEGF) (such as VEGF-A, VEGF-B, VEGF-C, VEGF-D and VEGF-E), Connective tissue growth factors (CTGF) (such as CTGF-1, CTGF-2, and CTGF-4), Growth differentiation factors (GDFs) (such as GDF-1, GDF-2, GDF-3, GDF-7, GDF-10, GDF-11, and GDF-15), cartilage-derived morphogenic proteins (CDMPs) (such as CDMP-1 and CDMP-2), LIM mineralization proteins (LMPs) (such as LMP-1, LMP-2, and LMP-3) and combinations thereof.

In a further embodiment, the hydrogel may be distributed throughout the scaffold in a gradient. This embodiment may comprise the scaffold having an increase amount of the hydrogel in the superficial zone, and less or no hydrogel in the deep zone. This embodiment is based on the simultaneous events of cartilage matrix synthesis and scaffold degradation that result in articular cartilage tissue regeneration. In native articular cartilage, cells in the superficial zone are flat and immature while in the intermediate zone they are rounder and express type II and type IX collagens. Cells in the deep zone are mature to hypertrophic. Use of a hydrogel gradient can help to control zonal differentiation state. For example, this embodiment may permit decreasing or increasing cellular exposure to growth factors in transition from the superficial to the deep zone. In one embodiment, this is achieved by having a growth-factor containing hydrogel (which may also encapsulate cells of interest) that is more abundant at the top superficial side and less abundant in the dense deeper zone. Alternatively, the amount of growth factor can vary within a hydrogel placed within the scaffold.

The scaffolds may comprise any other suitable materials as deemed appropriate for a given purpose, including but not limited to antibiotics and immunosuppressive agents. Examples of antibiotics useful with the biocompatible composite material include, but are not limited to, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamethoxazole, and vancomycin. Suitable immunosuppressive agents that can be included in the biocompatible composite material, include but are not limited to, steroids, cyclosporine, cyclosporine analogs, cyclophosphamide, methylprednisone, prednisone, azathioprine, FK-506, 15-deoxyspergualin, and other immunosuppressive agents that act by suppressing the function of responding T cells. Other immunosuppressive agents include, but are not limited to, prednisolone, methotrexate, thalidomide, methoxsalen, rapamycin, leflunomide, mizoribine, brequinar, deoxyspergualin, and azaspirane (SKF 105685), Orthoclone (muromonab-CD3) cyclosporine, tacrolimus, mycophenolate motefil, of which the active metabolite is mycophenolic acid), azathioprine, glucocorticosteroids, adrenocortical steroids such as prednisone and prednisolone, methotrexate, methoxsalen, and sirolimus.

In a second aspect, the present invention provides methods for making a gradient porous scaffold, comprising:
(a) mixing a plurality of microspheres with porogen in a desired ratio to produce a mixture, wherein the mixing comprises,
   (i) mixing the plurality of microspheres with different ratios of porogen to produce a plurality of mixes;
   (ii) combining the plurality of mixes to produce the mixture, such that a ratio of the porogen increases along a length of the mixture;
(b) sintering the mixture for a suitable time and under suitable conditions to bond adjacent microspheres, producing a sintered mixture; and
(c) leaching porogen from the sintered mixture to produce a gradient porous scaffold.

The methods of the invention can be used to create the gradient porous scaffolds of the first aspect of the invention. Scaffold porosity and mechanical properties can be tuned according to the clinical requirement by controlling the size and amount of the porogen added during the fabrication process. Through this method, we have improved microsphere performance and its ability to support osteoblast cell survival, proliferation and mineralization throughout the construct, and yet retain mechanical compatibility for effective bone regeneration.

The porosity and accessible volume of the scaffolds corresponded to porogen size and amount used. For example, as shown in the examples that follow, by mixing 40% NaCl and 60% PLGA microspheres (by dry weight), percent accessible pore volume increased 337% in relation to control scaffolds at an average pore size of 200 μm. Data and images describing scaffold pore volume are presented as a function of pore size, providing direct measurements of externally accessible pore space through the full range of diametral pore dimension. Although the range of pore size dimensions remained constant, the volume of porosity increased with higher concentration of porogen. Thus, as porogen concentration increased, the accessible interconnected volume also increased.

All embodiments and combinations of embodiments disclosed in the first aspect of the invention can be used in this second aspect of the invention. Any suitable microspheres can be used, including but not limited to the biodegradable microspheres disclosed herein. The microspheres can be prepared using any suitable technique, or purchased from commercial suppliers. In one embodiment, the biodegradable polymer comprises, consists essentially of, or consists of poly (lactic acid-glycolic acid) (also referred to as poly (lactic-co-glycolic acid) or poly(lactide-co-glycolide acid) (PLGA). In one embodiment, the PLGA is 85:15 PLGA (referring to the molar ratio of lactic acid to glycolic acid). In another embodiment, the PLGA is 50:50 PLGA, 65:35 PLGA, and the like. The microspheres are spherical particles, with diameters in the micrometer range (i.e. 1 μm to 1000 μm). The diameters may be any that are suitable for an intended use of the scaffold. In one embodiment, the microspheres are 100 μm or greater in diameter (i.e., 100 μm, 150 μm, 200 μm, 250 μm, 300 μm, 350 μm, 400 μm, 450 μm, 500 μm, or greater in diameter. In another embodiment, the microspheres are between about 200 μm in diameter and about 700 μm in diameter.

Any suitable porogen may be used, including but not limited to inorganic salt (including but not limited to sodium chloride (NaCl)), crystals of saccharose, gelatine spheres, paraffin spheres, or combinations thereof. In one embodiment, the porogen comprises NaCl. Any suitable diameter of the porogen particles may be used as appropriate for an intended use of the resulting scaffold. In one non-limiting embodiment, the porogen diameter (such as an NaCl porogen) may be between about 100 μm in diameter and about 400 μm in diameter.

Similarly, any suitable weight percentage of the porogen to the microsphere can be used as suitable for an intended use. In one embodiment, weight (wt) % of porogen with respect to microsphere is between about 1 wt % to about 50 wt %; in other embodiments, between about 1 wt % to about 40 wt %; about 1 wt % to about 30 wt %; about 1 wt % to about 20 wt %; about 1 wt % to about 10 wt %; about 10 wt % to about 50 wt %; about 20 wt % to about 50 wt %; about 30 wt % to about 50 wt %; about 10 wt % to about 40 wt %; about 10 wt % to about 30 wt %; and about 10 wt % to about 20 wt %. In one embodiment the weight (wt) % of NaCl porogen with respect to PLGA microspheres is between about 10 wt % to about 20 wt %.

The plurality of microspheres is mixed with different ratios of porogen to produce a plurality of mixes. As used herein, "different ratios of porogen" includes both (a) different amounts of a single sized porogen relative to microsphere amount; and (b) use of different sized porogens (i.e.: an increasing size of porogen, which may be an increasing size of the same type of porogen, or may comprise the use of different porogens which are of different size). The plurality of mixes is then combined to produce the mixture such that a ratio of the porogen increases along a length of the mixture; this can be carried out by any suitable technique. In one embodiment, the plurality of mixes can be automatically combined to produce a gradient structure. In another embodiment, the mixes are layered such that a ratio of the porogen increases along a length of the mixture. In one embodiment, the mixing comprises separately mixing the microspheres with each different ratio of porogen to produce the plurality of mixes, and then layering each separate mix into a mold for sintering. By way of non-limiting example, microspheres can be combined with 0, 5, 10, 20, and 40 weight percent porogen of a given diameter. The size of the porogen particles will dictate the size of the scaffold pores, while the polymer to porogen ratio directly correlates to the amount of porosity of the final structure. Gradient scaffolds can then be fabricated by sequentially adding the different polymer-porogen mixes, layer-by-layer, into a desired scaffold mold, followed by sintering to produce a sintered mixture and leaching of the porogen out of the sintered mixture to produce the gradient porous scaffold.

The method comprises the use of at least two different ratios of porogen to produce the mixes, and thus the combining comprises combining at least two mixes. As will be understood by those of skill in the art, any number of different ratios of porogen relative to the microspheres can be used (e.g., 2, 3, 4, 5, 6, or more) with a corresponding number of mixes. The number of different ratios/layers will depend on the intended use of the resulting gradient porous scaffold.

The sintering process can be carried out by any means suitable to join the microspheres, including but not limited to thermal sintering and liquid sintering, with liquid sintering being preferable for scale-up and compatible with a wider range of polymers. Sintering can be carried out for any time and under any conditions suitable to join the microspheres, and will depend at least in part on the composition of the microspheres. Determining appropriate sintering conditions will be well within the level of those of skill in the art based on the teachings herein.

In one embodiment, liquid sintering is used, wherein the liquid comprises a solvent/non-solvent composition appropriate for the polymer used. A "solvent/non-solvent composition" is a solvent system having at least two fractions: a volatile organic fraction (the solvent) and a non-volatile, typically aqueous, fraction. Any solvent/non-solvent composition suitable for the microspheres can be used. In one embodiment, the solvent/non-solvent composition has an organic solvent fraction and an aqueous (non-solvent) fraction. Appropriate solvent fractions include, but are not limited to, acetonitrile, acetone, hexanes, dichloromethylene, methanol, ethanol, and methylethylketone. Solvent/non-solvent compositions include acetone:water (e.g. 3:1) and acetonitrile:water (e.g. 8:1).

Once the sintering process is complete, the sintered mixture is leached to remove porogen. Such leaching can be by any means suitable to remove the porogen used. It is well within the level of those of skill in the art to determine an appropriate leaching technique based on the teachings herein and the specific porogen to be used. In one non-limiting embodiment, the porogen comprises NaCl and the leaching comprises soaking the sintered mixture in water for a time and under conditions suitable to dissolve the NaCl from the sintered mixture. Leaching of the porogen from the sintered mixture produces the gradient porous scaffolds of the invention.

The resulting scaffold may be of any suitable size or shape for an intended purpose. As will be understood by those of skill in the art, any size or shape scaffold can be made by using an appropriate mold. In one non-limiting embodiment, the scaffold comprises a cylindrical shape. In a further non-limiting embodiment, scaffolds can be made of sizes as discussed above.

In one embodiment, the methods may further comprise introducing a gel, including but not limited to a hydrogel into the porous scaffold. The gel or hydrogel can be any gel or hydrogel suitable for an intended use, including but not limited to those described above. In a further embodiment, the methods may comprise incorporating cells and/or growth factors into the scaffold and/or gel (such as a hydrogel). The gel/hydrogel is incorporated into the scaffold after the leaching process using any suitable technique. In one non-limiting embodiment, the gel/hydrogel is infused into the pore spaces of the scaffold. It is well within the level of those of skill in the art to determine an appropriate technique to introduce the gel/hydrogel and optional cells/growth factor into the completed scaffold, based on the teachings of the present invention.

In a third aspect, the present invention provides methods for bone regeneration or osteochondral defect repair, comprising transplanting a gradient porous scaffold of the invention into a subject in need thereof, so as to effect bone regeneration or osteochondral defect repair in the subject.

Large area or critically sized bone defect repair via scaffold-based bone tissue engineering requires a mechanically-stable scaffold that supports osteogenesis entirely (i.e., periphery and interior). For this, it is critical to develop a scaffold that allows for oxygen diffusion, and thus, cell survival and proliferation in the scaffold's interior regions. This requirement is met through use of the gradient porous scaffolds of the present invention.

Osteochondral defects cover subchondral bone and cartilage regions with a gradual change in the tissue structure from bone to cartilage. Previously fabricated scaffolds for osteochondral repair have shown limited success due to their failure to mimic the zonal structure of native tissue. In contrast, the gradient porous scaffolds of the present invention provide a regenerative engineering approach for bone and cartilage defect repair that mimic both the native articular cartilage structure and the underlying bone. The scaffolds of the invention 1) provide a stiff structural support for bone regeneration and a soft matrix for chondroprogenitor implantation; 2) can release suitable growth factors as appropriate; and 3) provide a gradient porous structure in combination with a hydrogel to encapsulate cells and serve as a vehicle for controlled growth factor release.

As used herein, "treating" means to provide a clinical benefit to a subject in need of bone regeneration or osteochondral defect repair.

The subject may be any mammal, such as a human subject. The subject may be in need of bone regeneration or osteochondral defect repair due to traumatic injury, osteoarthritis, post-traumatic osteoarthritis, osteochondral lesions, bone cancer, loss of tissue because of tumor resection, birth defects, to help fusion between vertebrae, correct deformities, and provide structural support to an injured spine or other bone. In one embodiment the method includes surgical excising a section of damaged bond and implanting the bone scaffold of sintered polysaccharide microspheres. The scaffold may be held in place with external stabilization devices, for example surgical pins, plates or screws. Depending on where the scaffold implantation is located and the size of the graft, an additional blood supply may be required. For these types of grafts, extraction a section of blood vessels from another part of the patient's body or from a donor and implantation along the implanted scaffold may be required.

In one embodiment, the gradient porous scaffold comprises a hydrogel within the scaffold, including but not limited to any of the hydrogels disclosed herein. Similarly, the methods may comprise use of a scaffold further comprising cells and/or growth factors associated with the scaffold. Any suitable cells and growth factors can be used as appropriate for an intended use of the scaffolds. In one embodiment, the cells may comprise stem cells, osteoblasts, chondrocytes, precursors thereof, and combinations thereof. In another embodiment, the growth factors may comprise bone morphogenetic protein (BMP) (including but not limited to BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; and BMP-18), Cbfa 1, insulin-like growth factors, interleukin-1, interleukin-6, tumor necrosis factor, Wnt5a, fibroblast growth factor (FGF) (such as FGF2), transforming growth factors (TGFs) (including TGF-$\beta$1, TGF-$\beta$2, and TGF-$\beta$3), Vascular endothelial growth factors (VEGF) (such as VEGF-A, VEGF-B, VEGF-C, VEGF-D and VEGF-E), Connective tissue growth factors (CTGF) (such as CTGF-1, CTGF-2, and CTGF-4), Growth differentiation factors (GDFs) (such as GDF-1, GDF-2, GDF-3, GDF-7, GDF-10, GDF-11, and GDF-15), cartilage-derived morphogenic proteins (CDMPs) (such as CDMP-1 and CDMP-2), LIM mineralization proteins (LMPs) (such as LMP-1, LMP-2, and LMP-3) and combinations thereof.

In a further embodiment, the hydrogels for use in the methods of the invention may be distributed throughout the scaffold in a gradient. This embodiment may comprise the scaffold having an increase amount of the hydrogel in the superficial zone, and less or no hydrogel in the deep zone. This embodiment is based on the simultaneous events of cartilage matrix synthesis and scaffold degradation that result in native articular cartilage tissue regeneration. In native articular cartilage, cells in the superficial zone are flat and immature while in the intermediate zone they are rounder and express type II and type IX collagens. Cells in the deep zone are mature to hypertrophic. Use of a hydrogel gradient can help to control zonal differentiation state. For example, this embodiment may permit decreasing or increasing cellular exposure to growth factors in transition from the superficial to the deep zone. In one embodiment, this is achieved by having a growth-factor containing hydrogel (which may also encapsulate cells of interest) that is more abundant at the top superficial side and less abundant in the dense deeper zone. Alternatively, the amount of growth factor can vary within a hydrogel placed within the scaffold.

The scaffolds may comprise any other suitable materials as deemed appropriate for a given purpose, including but not limited to antibiotics and immunosuppressive agents, including but not limited to those disclosed herein.

Example 1. Optimally Porous and Biomechanically Compatible Scaffolds for Bone Regeneration Large area or critically sized bone defects pose a serious challenge in orthopedic surgery, as all current treatment options present with shortcomings. Bone tissue engineering requires mechanically-stable scaffolds that support homogenous bone formation throughout the scaffold thickness. Despite advances in scaffold fabrication, current scaffold-based techniques are unable to support uniform, three-dimensional bone regeneration, and are limited to only the scaffold surface in vitro and in vivo. This is mainly due to inadequate scaffold pore sizes (<200 µm) and inadequate accessible pore volume, and the associated limited oxygen diffusion and vascular invasion.

In this example, we demonstrate a microsphere sintering and porogen leaching technique to fabricate scaffolds with increased accessible pore volume. Of the scaffolds developed, moderately-porous PLGA microsphere scaffolds were selected as most advantageous, since they retain mechanical strength in the range of human cancellous bone, and display significantly higher accessible pore volume, which is attributed to an increased percentage of larger pores (i.e., size range 200-600 µm). Unlike control scaffolds with limited pore size and accessible pore volume, moderately-porous scaffolds displayed increased oxygen diffusion, pre-osteoblast cell infiltration, proliferation, and survival throughout the entire scaffold. Furthermore, moderately-porous PLGA microsphere scaffolds displayed enhanced and homogenous mineralization in vitro. Since these moderately-porous scaffolds are weight-bearing, fully osteoconductive and have the ability to support vascularization, they can serve as effective scaffolds for large area bone defect repair/regeneration. In addition, the methods disclosed herein permit one to modulate scaffold porosity and in turn, develop oxygen tension controlled matrices that are effective for large area bone regeneration.

Methods and Materials
Microsphere Fabrication

PLGA microspheres were prepared by an oil-in-water method as reported previously (42). In brief, PLGA 85/15 (Lakeshore Biomaterials, Birmingham, Ala.) was dissolved in methylene chloride (L-14119, Fisher Scientific, Pittsburgh, Pa.) in a 1:5 dilution ratio (i.e., 4 g PLGA:20 milliliters of methylene chloride). The PLGA/methylene chloride solution was added slowly to 1 liter of 1% polyvinyl alcohol (PVA, Sigma-Aldrich, St. Louis, Mo.) solution under a stirring speed of 250 RPM. The stirring continued for 24 hours to allow the methylene chloride to evaporate. The resultant PLGA microspheres were washed with distilled water, filtered, air-dried, sieved into different sizes, and stored in a desiccator until further use.

A schematic illustration of the exemplary method is shown in FIG. 1a. In brief, PLGA microspheres (diameter 425-600 µm) and a porogen, NaCl (diameter 200-300 µm), were mixed at specific weight ratios (i.e., PLGA:NaCl ratios of 100:0, 90:10, 80:20, 70:30, 60:40 and 50:50). The PLGA/NaCl mixture was then placed into a steel mold, and thermally sintered at 100° C. The NaCl porogen was leached out by soaking the composite PLGA/NaCl scaffolds in distilled water for 2 hours, resulting in scaffolds with increased porosity compared to control scaffolds. The scaffolds with 0% NaCl are referred to as control PLGA scaffolds, while the rest as macro-porous scaffolds. We fabricated disc-shaped scaffolds (10 mm diameter, 2 mm height) for porosity measurements and the majority of cellular studies, and cylinder-shaped scaffolds (5 mm diameter, 10 mm height), which were utilized for mechanical testing, live/dead study, and part of mineralization studies. Scaffolds were air-dried and stored in a desiccator until future use. Scanning electron microscopy (SEM) was used to image the morphology of the microsphere scaffolds and visually examine the increased number of large pore sizes after NaCl-leaching.

Evaluation of Scaffold Porosity

Scaffold specimens were imaged using cone beam microfocus X-ray computed tomography to render three-dimensional models for direct quantitation of porosity (µCT40™, Scanco Medical AG, Bassersdorf, Switzerland). Serial tomographic images were acquired at 45 kV and 177 µA, collecting 2000 projections per rotation at 300 msec integration time. Three-dimensional 16-bit grayscale images were reconstructed using standard convolution back-projection algorithms with Shepp and Logan filtering, and rendered within a 12.3 mm field of view at a discrete density of 4,629,630 voxels/mm3 (isometric 6 µm voxels). Segmentation of solid scaffold from open porosity was performed in conjunction with a constrained Gaussian filter to reduce noise, applying a threshold of −220 Hounsfield units (water=0, air=−1000). Direct measurements of internal porosity included volume fraction, size, connectivity, accessible internal pore volume, and accessible solid surface area of scaffold (as a function of pore dimension). The accessible volume and surface parameters provide direct measurements of the pore volume and surface available to cell infiltration as a function of minimum pore dimension, using a distance transformation algorithm similar to Moore et al. (43)

Mechanical Testing of PLGA Microsphere Scaffolds

Compressive testing of cylindrical PLGA microsphere scaffolds (5 mm diameter×10 mm height, n=6/group) was performed at 2 mm/min (model 5544, Instron Corp., Norwood, Mass.) following the standard protocol of ASTM 1621 (44). Compressive strength was defined as the maximum stress magnitude. Apparent modulus was measured as the tangential slope of the linear region of the effective stress-strain curve at 50% of compressive strength magnitude.

MC3T3-E1 Pre-Osteoblast Cell Culture

The pre-osteoblast immortalized cell line MC3T3-E1 (American Type Culture Collection, Manassas, Va.) were cultured in α-minimal essential medium (α-MEM) containing 10% fetal bovine serum and 1% penicillin/streptomycin at 37° C., 5% $CO_2$ and 95% humidified air. Cells were maintained in sub-confluent cultures until needed for in vitro scaffold studies.

Cell Seeding and Culture on Scaffolds

PLGA microsphere scaffolds were sterilized by immersing the scaffolds in 70% ethanol for twenty minutes. Scaffolds were then washed three times in sterile PBS before exposing them to UV radiation for one hour. After cell trypsinization, a MC3T3 cell suspension containing $4 \times 10^4$ cells was uniformly seeded onto the scaffolds. The disc-shaped scaffolds were placed flat on the culture plate, and a 20 μl cell suspension was uniformly added to the top of the scaffold. The cylinder-shaped scaffolds were placed along the length of the scaffold on the culture plate, and a 40 μl cell suspension was added to the lengthwise surface as the scaffold was slowly rotated (i.e., along the long axis of the scaffold) to maintain uniform cell seeding. The cell-seeded scaffolds were incubated for two hours at 37° C. to allow for cell adhesion onto the scaffolds. The cell-scaffold constructs were cultured in osteogenic media (i.e., α-MEM supplemented with 10% FBS, 1% penicillin-streptomycin, 3 mM β-glycerophosphate and 50 μg/ml ascorbic acid), and maintained for 7, 14, 21, and 28 days in an incubator at 37° C., 5% $CO_2$, and 95% humidified air.

Cell Seeding Efficiency

After 6 hours of cell seeding, scaffolds were transferred to new wells. Cells at the bottom of the original wells were trypsinized, resuspended and counted with a hemacytometer. Cell seeding efficiency (i.e., the number of cells that adhered to the scaffolds) was determined by the difference between the number of cells initially seeded (i.e., $4 \times 10^4$ cells) and the number of cells that were counted at the bottom of the well.

Cell Proliferation on Scaffolds

DNA concentration of the pre-osteoblast MC3T3 cells cultured on control PLGA scaffolds and PLGA scaffolds with increased porosity (n=3) was evaluated quantitatively using Quant-iT™ PicoGreen™ dsDNA assay (Invitrogen, Carlsbad, Calif.) as reported previously (45). After culturing the samples (scaffold dimensions 8 mm diameter×2 mm height) for 7, 14, and 21 days in osteogenic media, the cell scaffold samples (n=3) for each experimental group were harvested. Samples were washed with PBS, incubated in lysis buffer (i.e., 1% Triton X-100 solution), and subjected to freeze-thaw cycles. DNA concentration from the cell lysates was determined according to the manufacturer's protocol. Experimental groups included control scaffolds (i.e., 0:100 ratio of NaCl:PLGA), and scaffolds with increased porosity (i.e., 10:90, 20:80, 30:70, and 40:60 ratio of NaCl:PLGA).

Cell Viability on Surface and Interior of Scaffolds

The live-dead cell viability assay used (Invitrogen, Carlsbad, Calif.) includes calcein AM and ethidium homodimer-1 probes to label live and dead cells green and red, respectively. We used this live-dead assay to compare MC3T3 cell survival on the surface and in the interior of scaffolds. Cylindrical scaffolds (5 mm diameter, 10 mm height) were cultured for 4, 7, and 14 days in osteogenic media, at which point the scaffolds (n=3) for each experimental group were harvested. Samples were bisected lengthwise from each scaffold group to allow for the examination of cell viability in the sample interior. Live-dead cell viability assay was performed according to the manufacturer's protocol, using confocal microscopy to image cells at the surface and interior of the scaffolds.

Cell Localization and Expression

To visualize cellular localization and expression via histology and immunohistochemistry, samples were paraffin-embedded and sectioned (46). Briefly, cell-scaffold constructs were washed with PBS, and then fixed in formalin overnight at 4° C. Samples were dehydrated sequentially using an isopropyl alcohol series (i.e., 70%, 90% and 100%) for one hour each, at room temperature. Samples were directly transferred to molten paraffin (Tissue Path Paraplast™ Tissue Embedding Media, Fisher Scientific, Pittsburgh, Pa.) at 55° C. for 10 minutes and then embedded in fresh molten paraffin. Paraffin-embedded samples were cut into serial sections (20 μm thick) using Cryofilm (Section-Lab Co. Ltd., Hiroshima, Japan) and a microtome sectioning machine. Sections were placed on glass slides for histological analysis. Sections were stained with Gill's 3 hematoxylin (Sigma-Aldrich, St. Louis, Mo.) to visualize MC3T3 cell localization within the PLGA scaffolds after culturing the constructs for 28 days in osteogenic media. Immunostaining of two bone markers, osteopontin (OPN) and collagen Type I (Col I) was performed via a rabbit polyclonal anti-human osteopontin (Abcam, Cambridge, Mass., ab8448) antibody and a rabbit polyclonal anti-human collagen type I antibody (Abcam, Cambridge, Mass., ab292), respectively. Briefly, sections were de-paraffinized in HistoClear™ (National Diagnostics, Atlanta, Ga.), taken through a descending series of ethanol concentrations, rehydrated in distilled water, and then placed in 3% hydrogen peroxide (Sigma-Aldrich, St. Louis, Mo.) in PBS to quench endogenous peroxidase activity. To improve antigen exposure, the sections were boiled in Target™ retrieval (Dako, Carpinteria, Calif.) and washed in distilled water. Samples were incubated with blocking solution (i.e., 0.5% (w/v) bovine serum albumin in PBS) for one hour. Primary antibodies were diluted in 0.5% (w/v) bovine serum albumin in PBS at concentrations of 1:200 for OPN or 1:300 for Col I. Samples were incubated with the primary antibody for two hours at room temperature. Sections were washed free of primary antibody and incubated with SignalStain® Boost IHC Detection Reagent, HRP, Rabbit (Cell Signaling, Boston, Mass., #8114) followed by an incubation with 3,3'-diaminobenzidine (DAB, Vector Laboratories, Burlingame, Calif.) for thirty seconds. The slides were rinsed three times in water, and mounted using mounting media (Electron Microscopy Sciences, Hatfield, Pa.) for thirty minutes.

Scaffold Mineralization Potential

Matrix mineralization or calcium deposition was evaluated via Alizarin Red™ staining. This colorimetric analysis is based on solubility of the red matrix precipitate with cetylpyridinium chloride (CPC, Sigma-Aldrich, St. Louis, Mo.) to yield a purple solution. Briefly, after 14, 21 and 28 days of culturing in osteogenic media, cell-scaffold constructs were washed with distilled water and fixed with 70% ethanol at 4° C. for one hour. Ethanol was removed and samples were air-dried for ten minutes. Samples were incubated with Alizarin Red™ dye (Sigma-Aldrich, St. Louis, Mo.) for ten minutes at room temperature. Following washes to remove excess dye, the samples were incubated with 10% CPC at room temperature for thirty minutes. The absorbance of the resulting solution, which is proportional to the amount of calcium deposited, was read on a TECAN™ plate reader at 562 nm.

Oxygen Tension Measurements

After culturing the MC3T3-E1 cells on control and macro-porous PLGA scaffolds for 28 days in osteogenic media, the cell-scaffold samples were quantitatively evaluated for the oxygen tension in the interior region of each sample group using needle-type fiber optic oxygen microsensors (501656, World Precision, Saratoga, Fla.), as previously described by Volkmer et al. (25) Specifically, we examined scaffold groups with 0%, 10%, 20%, 30%, and 40% NaCl, and cultured 50,000 cells on each scaffold (dimensions 5 mm diameter×10 mm height). The oxygen sensors were mounted on optic fibers with a tip diameter of 50 µm. To protect these fragile sensors, they are fixed within a standard hollow 27 gauge needle of 0.4-mm diameter. A 25 gauge needle was utilized to pre-form a 2.5 mm deep channel on the side of the scaffold for which the probe would then be inserted (305127, Becton Dickinson). Oxygen tension measurements in the medium were carried out by inserting a probe in the medium next to all experimental scaffold groups. Prior to sample measurements, the oxygen microsensor was calibrated following a conventional two-point calibration protocol described by the manufacturer. Briefly, oxygen-free water and water-vapor saturated air were used as calibration standards. The oxygen-free water standard was prepared by dissolving one gram of sodium sulfite (S430, Fisher Scientific) in 100 milliliters of water in a sealed vessel, and the water-vapor saturated air was prepared by placing a wet piece of cotton in a sealed vessel. The oxygen tension measurements are expressed as the mean of three samples per scaffold group±standard deviation.

Statistical Analysis

For cell seeding efficiency, cell proliferation, and mineralization assays a Two-way analysis of variance (ANOVA) was performed to compare data. Three scaffolds per group were analyzed at each time point. Error is reported in figures as the standard deviation (SD) and significance was determined using a probability value of $P<0.050$.

Results

Microsphere Scaffolds with Increased Porosity

PLGA microsphere sintering often results in three-dimensional scaffolds with limited pore volume (42). However, we developed a novel method to fabricate PLGA microsphere scaffolds with increased pore volume and average pore size, as shown in FIG. 1A. Through mixing a porogen (i.e., NaCl crystals, 200-300 µm diameter) with PLGA microspheres (425-600 µm diameter), thermal sintering, followed by porogen leaching, we successfully created PLGA microsphere scaffolds with increased pore volume. SEM imaging demonstrated that after porogen leaching (FIG. 1D), there was visually an increase in number of large pore sizes compared to scaffolds fabricated with PLGA microspheres alone. (i.e., control PLGA scaffolds).

Scaffold Porosity Via Micro-CT

Micro-CT imaging was used to reconstruct 3D models of scaffolds for nondestructive measurements of porosity. Computational assessment of all Micro-CT images confirmed that the internal porosity is one interconnected space comprising 99.9% of the total pore volume. The porosity and accessible volume of the PLGA microsphere scaffolds corresponded to porogen size and amount used. For example, by mixing 40% NaCl and 60% PLGA microspheres (by dry weight), percent accessible pore volume increased 337% in relation to control scaffolds at an average pore size of 200 µm (FIG. 2D). Data and images describing scaffold pore volume are presented as a function of pore size, providing direct measurements of externally accessible pore space through the full range of diametral pore dimension (FIGS. 2A-C and 3). Although the range of pore size dimensions remained constant, the volume of porosity increased with higher concentration of porogen. For example, blue areas signify the accessible volume in the scaffolds to objects with a diameter in the range of 100-200 µm, and red in the range of 400-500 µm. Thus, as porogen concentration increased, the accessible interconnected volume also increased (FIG. 2A-D). In control scaffolds, a sphere with a diameter of 200 µm can access approximately 10% of the total pore volume, whereas the same sphere can access approximately 40% of the pore volume of the 40% NaCl/60% PLGA scaffold. This is illustrated in FIG. 3, which again shows that the experimental scaffolds fabricated with a porogen have a higher percentage of accessible pore volume in the 300-500 µm range in comparison to control scaffold. Thus, we effectively increased the accessible volume for cell infiltration throughout the scaffold.

Scaffold Mechanical Characterization

Figure 4:
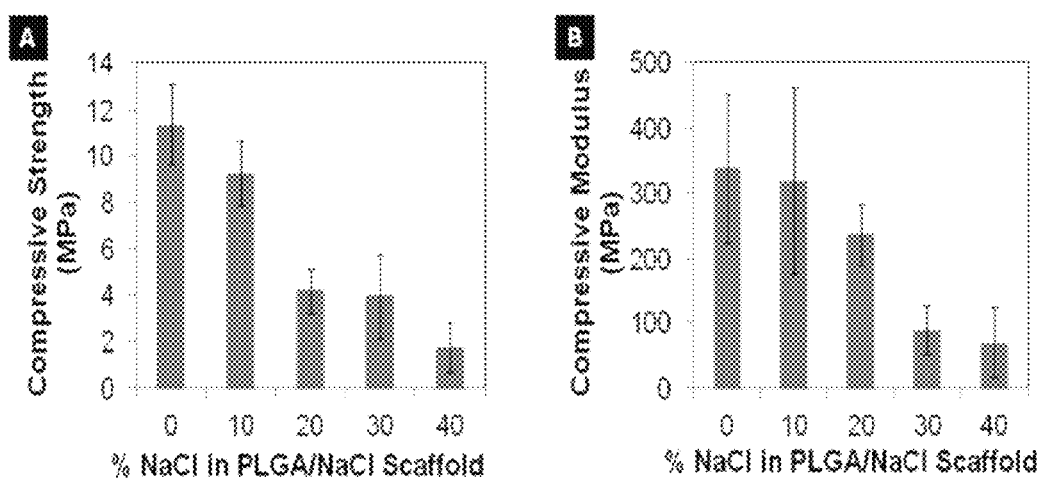
FIG. 4. Mechanical characterization of PLGA microsphere scaffolds with increased porogen content. Analysis of (A) compressive strength and (B) compressive modulus.

By using an increasing amount of porogen in the scaffold fabrication process, compressive strength and modulus of the scaffolds were sacrificed (FIG. 4). Scaffolds with increased porosity (i.e., 40% NaCl/60% PLGA by dry weight) displayed significantly less compressive strength and modulus than control scaffolds (i.e., 0% NaCl/100% PLGA). Scaffolds with moderately-sized pores (i.e., 20% NaCl/80% PLGA) displayed a significant decrease, 63.2%, in compressive strength, and a 29.8% decrease in compressive modulus in comparison to control scaffolds. 20% NaCl/80% PLGA displayed significantly higher compressive strength, 140%, and modulus, 240%, than scaffolds with the highest porosity (i.e., 40% NaCl/60% PLGA). The compressive modulus and strength for the scaffolds with increased porosity (i.e., 10-40% NaCl/90-60% PLGA), although lower than the control scaffold, are in the range of human trabecular bone mechanical properties (i.e., compressive modulus 50-800 MPa and compressive strength 1-10 MPa (47). Thus, we termed the 20% NaCl/80% PLGA scaffold group as moderately-porous scaffolds, since they display significantly higher pore volume than control, while retaining mechanical strength.

Figure 5:
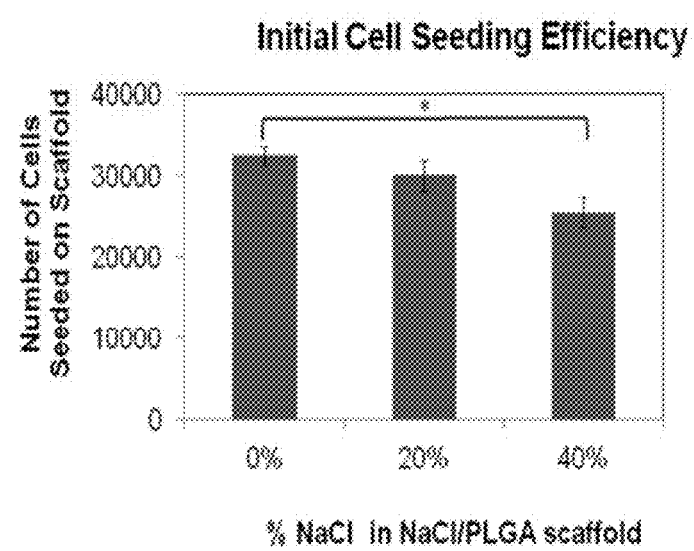
FIG. 5. Effect of increasing porosity on cell seeding efficiency on scaffolds. (*signifies $p<0.05$).
Figure 6:
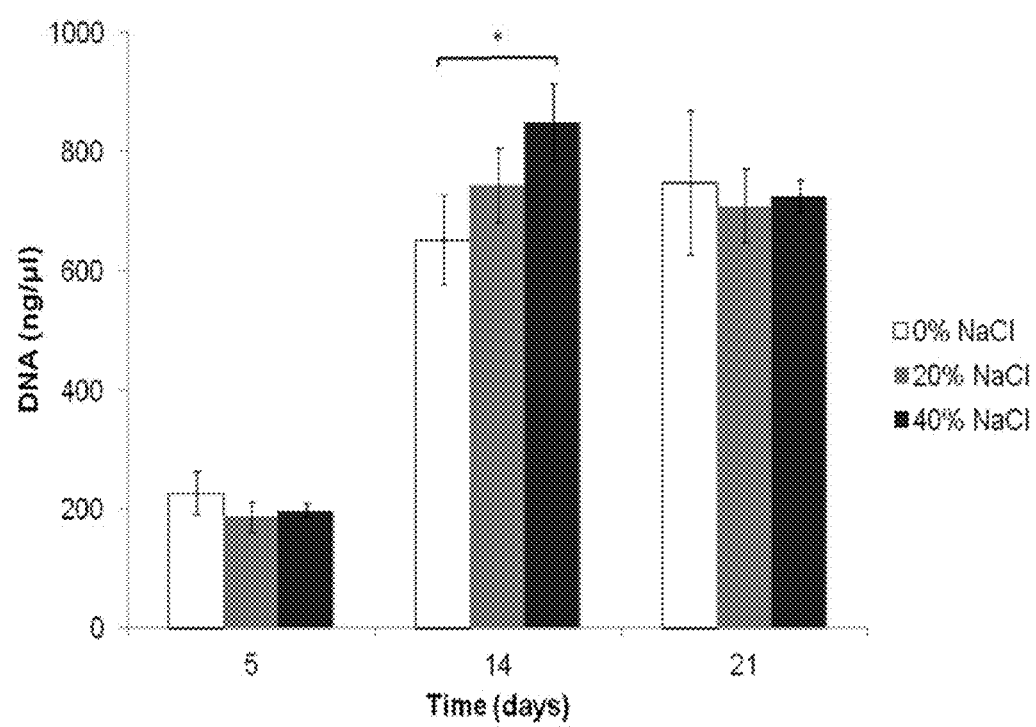
FIG. 6. Effect of increasing porosity on proliferation of murine pre-osteoblast cells (MC3T3-E1) seeded on PLGA control and moderately-porous scaffolds at 5, 14 and 21 days. (* signifies $p<0.05$).
Figure 7:
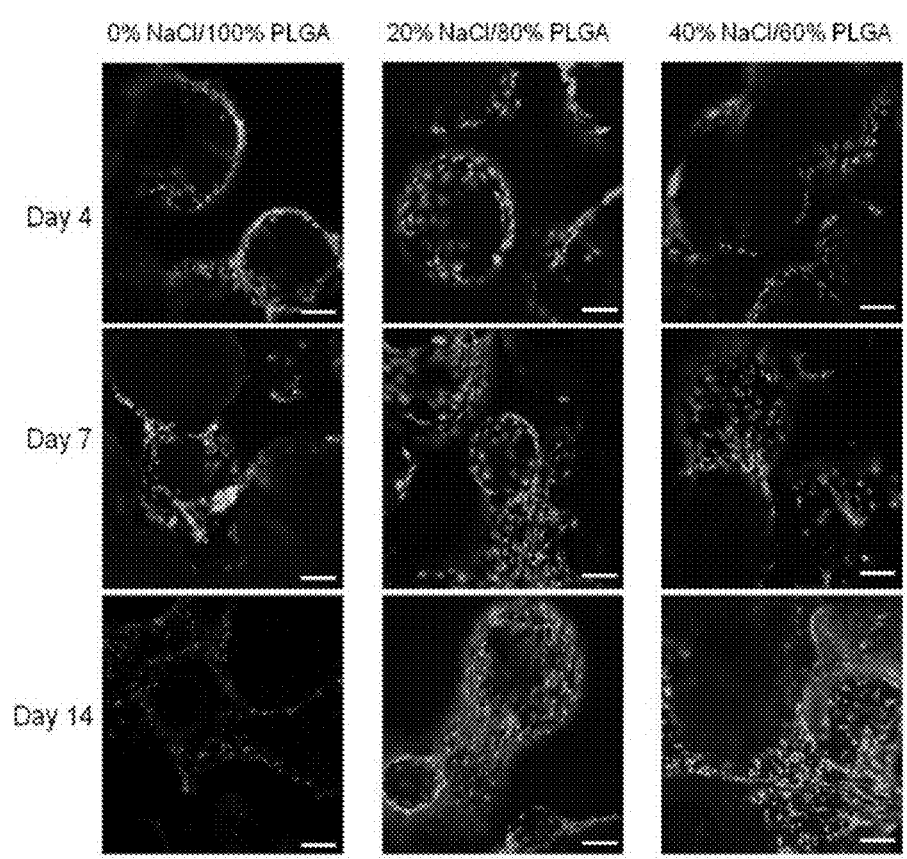
FIG. 7. Effect of increasing porosity on cell viability in the interior of the PLGA microsphere scaffolds at 4, 7, and 14 days (scale=200 μm).

Effect of Scaffold Accessible Pore Volume on Pre-Osteoblast Cell Infiltration, Proliferation and Survival The efficiency of initial cell seeding decreased with increasing porogen used to fabricate the PLGA microsphere scaffolds (FIG. 5). Of the $4 \times 10^4$ MC3T3 cells initially seeded onto each scaffold, approximately $3.3 \times 10^4$ cells adhered to the control scaffolds, and only $2.5 \times 10^4$ cells adhered to the scaffolds with increased porosity (i.e., 40% NaCl/60% PLGA by dry weight). However, after 5 days of culture in osteogenic media, the DNA concentration, which is proportional to cell number, was not significantly different in control scaffolds and scaffolds with increased porosity (i.e., 20% NaCl/80% PLGA and 40% NaCl/60% PLGA by dry weight). By 2 weeks of culture, cell number and proliferation in the scaffolds with increased porosity exceeded that of control scaffolds (FIG. 6). The limitation of cell culture on scaffolds was seen by 3 weeks of culture, as the capacity of the scaffolds to support cell proliferation began to decrease. The effects of scaffold porosity on cell viability were examined on the surface of the scaffolds, as well as the interior, of the scaffolds. At 4, 7, and 14 days of cultures, cell-scaffold constructs were bisected, and live/dead assays were performed. Representative fields from the center of the scaffold (approximately 5 mm depth) taken by confocal microscopy are shown in FIG. 7. After 4 days of culture, there was not a significant difference in live:dead cell ratio between the control scaffolds and scaffolds with increased porosity. By 14 days of culture, we observed a significant difference in live cells present in the interior region of scaffolds with increased porosity versus control scaffolds. In 20% NaCl/80% PLGA and 40% NaCl/60% PLGA scaffolds, the cells displayed a robust and healthy morphology, with extended processes. In contrast, the cells in the center of the control scaffolds were mostly dead by 14 days and displayed a round morphology appearance.

Cell Localization and Expression on PLGA Microsphere Scaffolds

Figure 8:
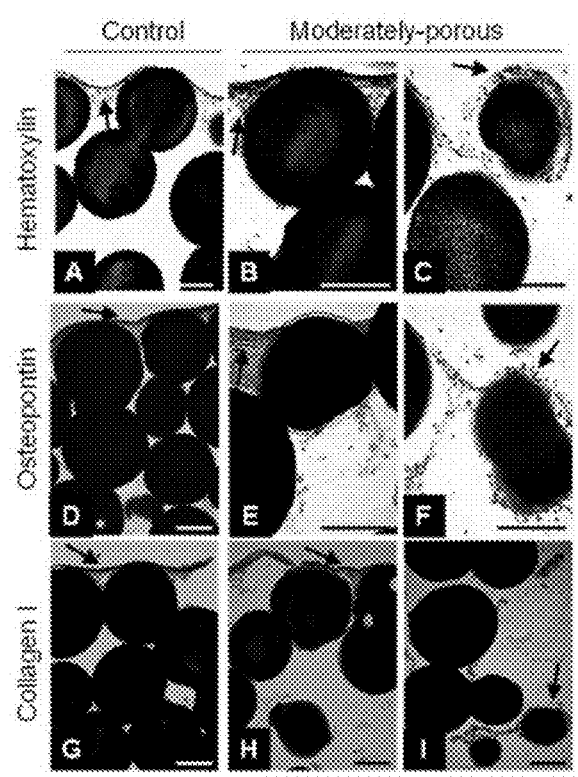
FIG. 8. MC3T3-E1 cellular localization and expression on control and moderately-porous PLGA scaffolds. Hematoxylin staining of control (A) and moderately-porous scaffolds (top (B) and center (C)), Osteopontin immunohistochemistry of control (D) moderately-porous scaffolds (top (E) and center (F)), and Collagen Type I immunohistochemistry of control (G) and moderately-porous scaffolds (top (H) and center (I)). Scale on all images=200 μm.

Through a modified paraffin-embedding and sectioning procedure, as described above, we were able to study the cellular localization and expression of the MC3T3 cells cultured on our PLGA microsphere scaffolds. In FIG. 8, PLGA scaffolds with increasing porosity (i.e., 20% NaCl/80% PLGA and 40% NaCl/60% PLGA; images of 40% NaCl/60% PLGA scaffolds are not shown) promote cell infiltration into the interior of the scaffolds. After 28 days of culturing MC3T3 cells on the scaffolds, hematoxylin staining highlighted cells densely located on the top of control scaffolds and not in the center of the control scaffolds (FIG. 8A). On the other hand, scaffolds with increased porosity displayed cell localization on the surface, as well as increased cell infiltration and survival in the center of the scaffold (FIGS. 8B, C). Likewise, we found cells expressing osteopontin and collagen type I only on the surface of the control scaffolds (FIGS. 8D, G). PLGA scaffolds with increased porosity displayed cells expressing osteopontin and collagen type I at the top, as well as the center of the scaffold (FIGS. 8E, F, H, I).

Effect of Scaffold Porosity on Mineralization

Figure 9:
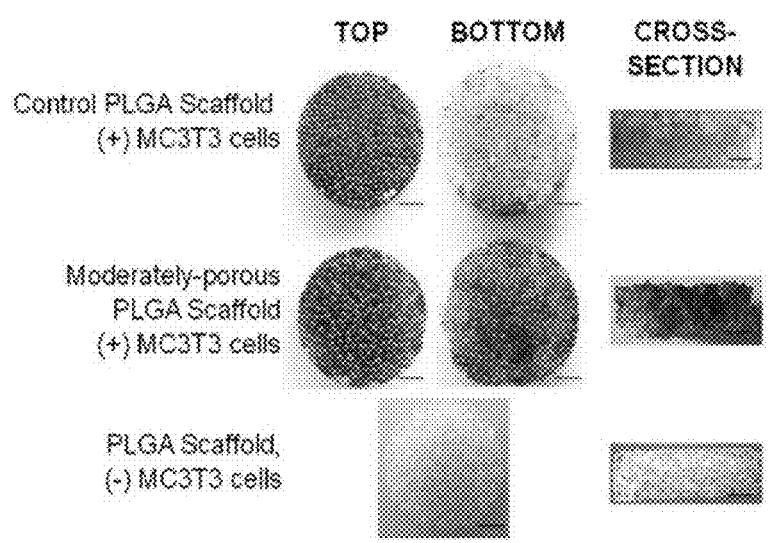
FIG. 9. Mineralization potential of control and moderately-porous PLGA microsphere scaffolds. Alizarin Red™ staining was performed after 28 days of MC3T3-E1 cells were cultured on scaffolds. Staining in images signifies mineralization or calcium deposition. Moderately-porous scaffold displayed mineralization on throughout the scaffold (i.e., top and bottom surfaces, and cross section), while control scaffold mineralization is limited to only top surface of the scaffold. Scale bar=1000 μm.
Figure 10:
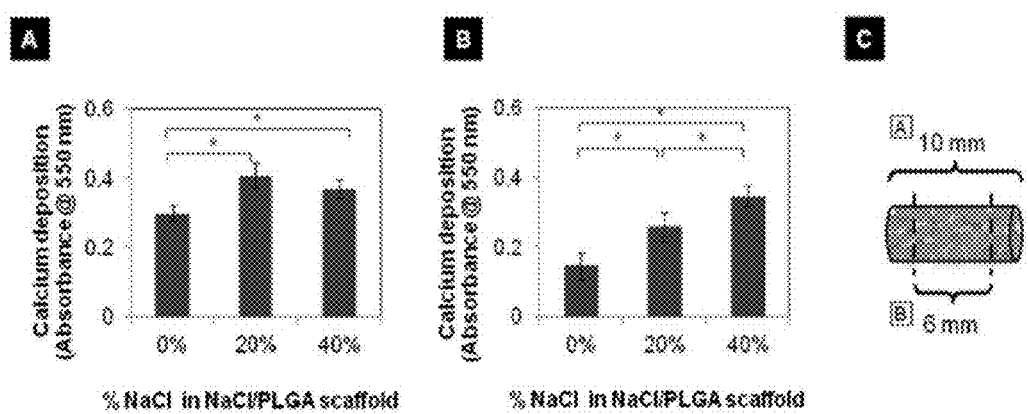
FIG. 10. Effects of porosity on mineralization (A) throughout the entire scaffold, and (B) in the center of the scaffold. After 28 days of cell culture on scaffolds, Alizarin Red™ staining was performed on the entire cell-scaffold construct and quantified. Two millimeters from the top and bottom surfaces of the scaffolds were manually removed as shown in (C), and Alizarin Red™ staining was performed to analyze the mineralization in the center of the constructs (B). (* signifies p<0.05).

After 28 days following seeding and culturing MC3T3 cells on scaffolds, we performed Alizarin Red™ Staining to detect calcium mineralization. Scaffolds with increased porosity visually appeared to have higher mineralization potential than control scaffolds (FIG. 9). Control scaffolds displayed mineralization limited to the top surface, and not in the center and bottom. On the other hand, scaffolds with increased porosity showed staining throughout the entire scaffold (i.e. top and bottom surfaces, and middle of construct). To compare and quantify the mineralization that was occurring throughout the scaffolds versus mineralization occurring only in the center of the scaffolds, we cultured MC3T3 cells on cylindrical scaffolds that were taller (scaffold size 10 mm height, 5 mm diameter), so that we were able to manually dissect 2 mm off the top and bottom scaffold surfaces (FIG. 10). Staining quantification confirmed the increase in mineralization in scaffolds with increasing porosity. 20% NaCl/80% PLGA scaffolds displayed the highest significant difference in mineralization compared to control. Although mineralization in 40% NaCl/60% PLGA scaffolds displayed higher mineralization potential than control scaffolds, it was not as high as 20% NaCl/80% PLGA (FIG. 10a). After manually removing the top 2 mm and bottom 2 mm surfaces of the tall cylindrical scaffolds, we quantified the mineralization in the center portions of the scaffolds. Mineralization increased significantly in the center of the scaffolds with increasing porosity after 28 days in culture (FIG. 10B).

Effect of Scaffold Porosity on Oxygen Levels in Scaffold's Interior

Figure 11:
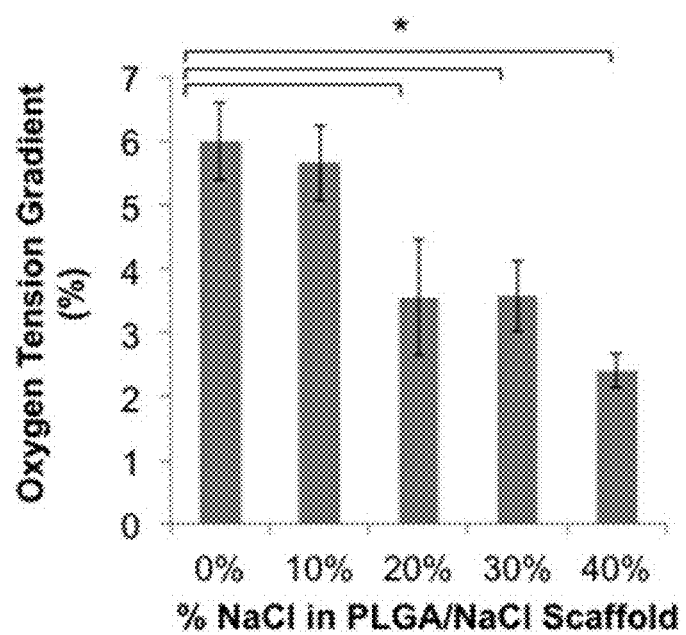
FIG. 11. The effect of porosity on oxygen tension gradient from the exterior to interior of PLGA microsphere scaffolds after 4 weeks in vitro. Oxygen tension of ambient air is 21%, and average oxygen tension of cell culture media is 6.67%±1.11%.

Oxygen tension measurements demonstrated a significant gradient between the media surrounding the cultured constructs and the interior regions of the constructs in all experimental groups after 4 weeks in vitro. Oxygen tension in the peri-construct region for all experimental scaffold groups was not statistically different from each other, and averaged 6.67%±1.11%. Oxygen tension in the interior of the cell-seeded scaffolds was directly related to the concentration of porogen used to fabricate the scaffolds. Specifically, increases in the scaffold's porosity facilitated and enhanced oxygen diffusion to the construct's interior region, and thus, decreasing the oxygen tension gradient from the scaffold's exterior to interior (FIG. 11). The peri-construct—interior construct oxygen gradient was most significantly seen in control scaffolds, where the oxygen gradient in the interior of cell-seeded control (0% NaCl/100% PLGA scaffolds) scaffolds conditions dropped below 1%. Moderately-porous scaffolds (20% NaCl/80% PLGA scaffolds) displayed similar oxygen tension gradients as compared to macroporous scaffolds (40% NaCl/60% PLGA scaffolds).

Discussion

Figure 2:
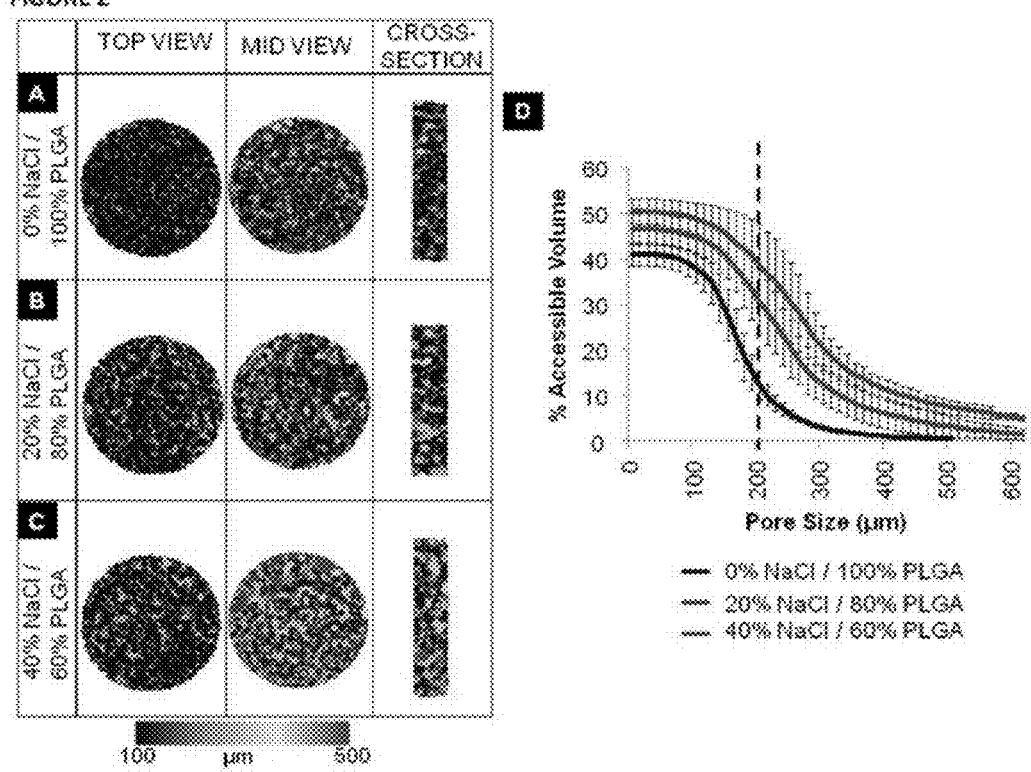
FIG. 2. Scaffold Pore Interconnectivity and Percent Accessible Volume obtained via Micro-CT imaging and analysis. Accessible volume space images generated by imposing specific pore diameter parameters (scale 100-500 μm) on (A) 0% NaCl/100% PLGA, (B) 20% NaCl/80% PLGA and (C) 40% NaCl/60% PLGA scaffolds from a top-view, mid-view and cross-sectional view. (D) Graph comparing the effect of increasing porogen to accessible volume in the PLGA scaffolds. Dashed line illustrates percent accessible volume of PLGA/0% NaCl and PLGA/40% NaCl scaffolds for an object with a diameter of 200 μm.
Figure 3:
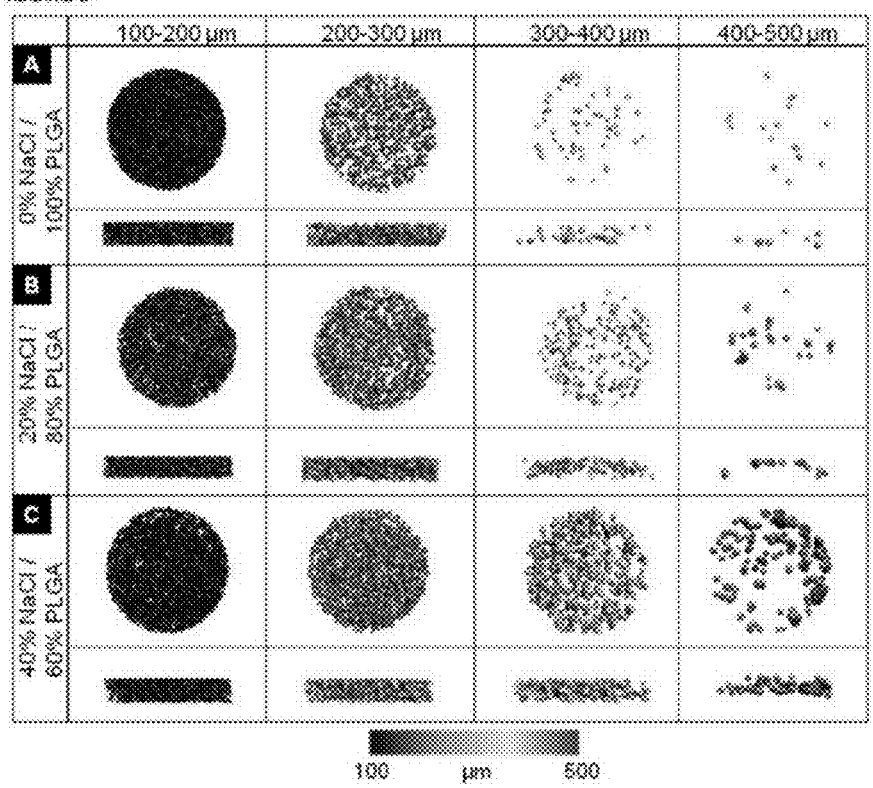
FIG. 3. Increasing scaffold accessible volume in moderately-porous PLGA scaffolds. Interconnected volume accessible to spherical objects with specific diameter range (i.e., 100-200 μm, 200-300 μm, 300-400 μm, 400-500 μm) in (A) PLGA/0% NaCl, (B) PLGA/20% NaCl, and (C) PLGA/40% NaCl.

Large area or critically sized bone defect repair via scaffold-based bone tissue engineering requires a mechanically-stable scaffold that supports osteogenesis entirely (i.e., periphery and interior). For this, it is critical to develop a scaffold that allows for oxygen diffusion, and thus, cell survival and proliferation in the scaffold's interior regions. In the present study, we have developed a novel biodegradable scaffold for bone regeneration that encompasses the previously mentioned requirements, and demonstrated their ability to promote uniform osteogenesis in vitro. Scaffold porosity can be mainly described in terms of its pore size and the amount of accessible pore volume. Increase in pore volume or pore size, or both can be attributed to the scaffold increased porosity. As seen in FIGS. 2 and 3, porogen leaching from microsphere scaffolds result in increased accessible pore volume with increased density of large pores. This is referred to increased porosity while describing the newly fabricated macro-porous scaffolds. Appropriate scaffold porosity and accessible volume are critical for obtaining effective osteogenesis in large area bone repair. Deviations from the moderate porosity range display positive and negative tradeoffs. Scaffolds with decreased average pore size are associated with an increase in surface area, and thus, cell seeding efficiency (48). Such scaffolds with relatively lower porosity exhibit higher mechanical strength, an important factor in clinical applications (49). However, these scaffolds are also associated with significant drawbacks. For instance, decreased accessible volume result in decreases in mass transport of oxygen and nutrients, and in turn, decreases in osteoblast survival, bone matrix remodeling, and regeneration (20). A delay in bone remodeling, which involves osteoclastic bone resorption followed by osteoblastic bone deposition, occurs as osteoclasts are inhibited from functioning maximally in scaffolds with low porosity (50). Further, the scaffold's porosity has a profound effect on the rate of vascularization (21, 51). In scaffolds with relatively low porosity, angiogenesis is not sufficiently observed, which causes an accumulation of metabolites and promotion of inflammation, and thus, suboptimal bone regeneration (52). On the other hand, scaffolds with high porosity are not as mechanically strong and display decreased cell seeding efficiency, but are associated with higher mass transport of oxygen and nutrients, facilitating osteogenic proliferation, and thus bone regeneration (53, 54). With respect to dynamic bone remodeling, increased osteoclast number and size in scaffolds with high porosity may result in increased bone matrix strength via increases in bone remodeling. Also, studies have identified scaffolds with average pore sizes greater than 300 microns to provide the most efficient vascularization and bone regeneration (55, 56).

For bone tissue engineering applications, PLGA scaffolds developed via microsphere sintering techniques have a unique advantage as they display mechanical properties in the range of human cancellous bone (38), a useful aspect of scaffolds to ensure proper support at the defect site upon implantation. These cancellous bone-mechanically compatible scaffolds are attractive since bone has the special ability to undergo remodeling and optimize its mechanical function for its particular skeletal location, and thus, can be effectively used for regeneration in either cancellous or cortical bone sites (57). Our group has fabricated and extensively investigated PLGA 85/15, PLGA-nano hydroxyapatite composites, and PLGA-chitosan blend microsphere scaffolds for bone regeneration (38, 58). PLGA 85/15 based microsphere scaffolds have supported bone forming cell proliferation, differentiation and mineralization in vitro and in vivo bone formation when implanted in a rabbit ulnar defect model (39, 40). However, these PLGA microsphere scaffolds lack the necessary porosity for sufficient cell in-growth, and thus, fail to provide the prerequisites required for optimal bone regeneration (i.e. a stable oxygen and nutrient supply). A common observation with these and other scaffolds with lower than the optimal accessible porosity result in surface-limited osteogenesis in vitro and in vivo (20, 40, 42). Studies have demonstrated scaffolds with increasing porosity to be directly associated with increasing osteoblast proliferation and differentiation throughout the entire scaffold, due to enhanced neo-vascularization and mass transport of oxygen and nutrient supply (21, 23-25). Thus, PLGA microsphere scaffolds with human bone-mechanical compatibility and increased porosity are desired as they will provide the prerequisites to optimal bone regeneration throughout the entire construct.

In a way, microsphere sintering is the same as sphere close-packing. In this process, the expected pore volume, or void fraction, are proportional to the sphere size. For microspheres of 425-590 µm size range, the resulting scaffolds showed a majority of the pores in the range of 100-200 µm (38). To effectively increase microsphere scaffold pore volume, we have used microsphere sintering followed by a porogen leaching method. In this method, we combined PLGA microspheres with a porogen (i.e., NaCl particles of varied sizes), thermally sintered, and then leached out the porogen by soaking the scaffold constructs in water (FIG. 1). Scaffold porosity and mechanical properties can be tuned according to the clinical requirement by controlling the size and amount of the porogen (i.e., NaCl) added during the fabrication process. Through this method, we have improved PLGA microsphere performance and its ability to support osteoblast cell survival, proliferation and mineralization throughout the construct, and yet retain mechanical compatibility for effective bone regeneration.

As we increase the dry weight ratio of NaCl:PLGA used during the fabrication process of PLGA microsphere scaffolds, the porosity and accessible volume increases significantly (Table 1). Accessible volume involves the pore spaces that are available from the top of the scaffold to the bottom. High accessible volume within scaffolds influences the efficiency of nutrient, gas, and waste exchange within the scaffolds, as well as cell migration and tissue in-growth needed to promote tissue regeneration. Furthermore, it facilitates angiogenesis allowing for blood vessel in-growth, and thus, increases supply of oxygen and nutrients to the center of the construct (43,59). However, with increases in pore volume, mechanical integrity is sacrificed (FIG. 4). Scaffolds with a higher ratio of NaCl than that in 40% NaCl/60% PLGA scaffolds were not mechanically stable. Scaffolds fabricated with an intermediate concentration of NaCl (i.e., moderately-porous scaffolds; 20% NaCl/80% PLGA microsphere scaffolds) were significantly more mechanically robust than those fabricated with 40% NaCl/60% PLGA. In addition to decreasing mechanical strength, scaffolds with increased porosity display a lower cell seeding efficiency, as these scaffolds are less efficient in retaining cells during the cell seeding process (FIG. 5). Despite the decrease in initial cell number seeded on the scaffolds with increased porosity, cell numbers on these scaffolds reached that of control scaffolds by 5 days in culture, and surpassed it by two weeks in culture (FIG. 6). Thus, scaffolds with larger porosity have a better potential to support cell proliferation in vitro, likely due to their ability to improve oxygen and nutrient transport, and waste removal throughout the entire scaffold-cell construct. Increased cell survival was confirmed via a cell viability assay, which showed significantly more live cells in the center of macro-porous scaffolds compared to that in control scaffolds with decreased porosity by two weeks in culture (FIG. 7). Scaffolds with higher porosity displayed robust cell survival and expression of osteopontin and collagen type I, two major bone markers (FIG. 8). In addition, mineralization potential throughout the entire scaffold-cell construct increased with an increase of porogen used in the scaffold fabrication process (FIG. 9). However, there appears to be a relationship between mineralization potential and surface area of scaffold since scaffolds with higher NaCl content than that of moderately-porous scaffolds (i.e., 40% NaCl/60% PLGA scaffolds) did not display as high of mineralization as for moderately-porous scaffolds. Specifically, moderately-porous scaffolds displayed 35% greater mineralization than control scaffolds, and scaffolds with the highest porosity (i.e., 40% NaCl/60% PLGA scaffolds) displayed approximately 23% increase over control, after 28 days of culturing MC3T3 cells on the scaffolds in osteogenic media. The increase in mineralization in scaffolds with increased porosity can be attributed to the mineralization occurring throughout the entire constructs, including the scaffold's interior regions (FIG. 10). Per these attributes, moderately-porous scaffolds display the highest performance in supporting cell infiltration, proliferation, and mineralization throughout the entire construct in vitro (Table 1) (41).

TABLE 1

Table 1. Porosity, mechanical performance and osteoconductivity comparison between control and moderately-porous PLGA microsphere scaffolds.

|  | Control Scaffold PLGA 85/15 | Moderately-Porous Scaffold (20% NaCl/80% PLGA 85/15) |
|---|---|---|
| Accessible Pore Volume | ~12% pore volume is with pore sizes ≥ 200 µm | ~31% pore volume is with pore sizes ≥ 200 µm |
| Mechanical Properties |  |  |
| Compressive Modulus | 338.4 ± 114.5 MPa | 237.4 ± 46.5 MPa |
| Compressive Strength | 11.4 ± 1.73 MPa | 4.19 ± 0.99 MPa |
| Cell Seeding Efficiency | 81.3% | 63.7% |

TABLE 1-continued

Table 1. Porosity, mechanical performance and osteoconductivity comparison between control and moderately-porous PLGA microsphere scaffolds.

| | Control Scaffold PLGA 85/15 | Moderately-Porous Scaffold (20% NaCl/80% PLGA 85/15) |
|---|---|---|
| Cell Proliferation | 1.87 fold increase from 5-14 day in vitro | 2.98 fold increase from 5-14 day in vitro |
| Cell Viability and phenotypic expression | Periphery limited | Homogeneous thoughout entire scaffold |
| Mineralization | Surface limited | Homogeneous throughout entire scaffold (i.e., top, center, bottom) 35.5% more mineralization in entire scaffold 79.2% more meneralization in scaffold's interior |
| Osteoconductivity | Surface limited | Fully osteoconductive |
| Oxygen Tension Gradient (Exterior - Interior) | 6.02% ± 0.77% | 2.42% ± 0.163% |

Our moderately-porous scaffolds stand superior to other methods currently utilized to increase cell proliferation and mineralization throughout BTE constructs in vitro. For instance, bioreactor culture methods are popular alternative methods utilized to increase cell infiltration and proliferation throughout constructs (60-64). However, unlike bioreactor culture methods, which are complex in nature and only effective in vitro, moderately-porous scaffold development is simple and effectively allows for enhanced oxygen tensions throughout the constructs both in vitro and in vivo. In addition, the increased porosity in moderately-porous scaffolds is expected to improve vascularization and osteoclast participation, and hence, bone remodeling by closely mimicking the native bone repair process (50). Lastly, studies have cicied a significant enhancement in bone regeneration when adding growth factors (i.e. BMP-2 and VEGF) to BTE constructs (65-68). However, functional bone regeneration may only occur when the entire construct, including the interior, supports cell survival and proliferation (i.e., fully osteoconductive). The combination of growth factors with an appropriate scaffold, such as our moderately-porous scaffold, that is fully osteoconductive and may support vascularization throughout, will lead to optimal bone regeneration in large area bone defects.

In this study, by controlling scaffold pore size and pore volume we effectively designed oxygen tension controlled matrices. Increasing the amount of porogen resulted in a systematic increase in not only porosity, but also available oxygen tension throughout the matrix. The enhanced survival, proliferation, differentiation and mineralization of pre-osteoblasts may be attributed to the increase in available oxygen tension. Thus, we can successfully enhance the bone regeneration potential of matrices in static culture via the design of these oxygen tension controlled matrices. Therefore, the proposed moderately-porous scaffolds with improved oxygen availability and bone compatible mechanical properties are desirable for large area bone regeneration, and can be used for large area/critical sized bone defect repair.

References for Example 1

1. Laurencin C, Khan Y, El-Amin S F. Bone graft substitutes. Expert Rev Med Devices. 2006; 3(1):49-57.
2. Pneumaticos S G, Triantafyllopoulos G K, Basdra E K, Papavassiliou A G. Segmental bone defects: from cellular and molecular pathways to the development of novel biological treatments. J Cell Mol Med. 2010; 14(11): 2561-9.
3. Luo J, Sun M H, Kang Q, Peng Y, Jiang W, Luu H H, et al. Gene therapy for bone regeneration. Curr Gene Ther. 2005; 5(2):167-79.
4. Laurencin C T, Ambrosio A M, Borden M D, Cooper J A. Tissue engineering: orthopedic applications. Annu Rev Biomed Eng. 1999; 1:19-46.
5. Greenwald A S, Boden S D, Goldberg V M, Khan Y, Laurencin C T, Rosier R N, et al. Bone-graft substitutes: facts, fictions, and applications. J Bone Joint Surg Am. 2001; 83-A Suppl 2 Pt 2:98-103.
6. Gazdag A R, Lane J M, Glaser D, Forster R A. Alternatives to Autogenous Bone Graft: Efficacy and Indications. J Am Acad Orthop Surg. 1995; 3(1):1-8.
7. Banwart J C, Asher Mass., Hassanein R S. Iliac crest bone graft harvest donor site morbidity. A statistical evaluation. Spine (Phila Pa 1976). 1995; 20(9):1055-60.
8. Arrington E D, Smith W J, Chambers H G, Bucknell A L, Davino N A. Complications of iliac crest bone graft harvesting. Clin Orthop Relat Res. 1996(329):300-9.
9. Tomford W W, Starkweather R J, Goldman M H. A study of the clinical incidence of infection in the use of banked allograft bone. J Bone Joint Surg Am. 1981; 63(2):244-8.
10. Lord C F, Gebhardt M C, Tomford W W, Mankin H J. Infection in bone allografts. Incidence, nature, and treatment. J Bone Joint Surg Am. 1988; 70(3):369-76.
11. Delloye C, Cornu O, Druez V, Barbier O. Bone allografts: What they can offer and what they cannot. J Bone Joint Surg Br. 2007; 89(5):574-9.
12. Nukavarapu S, Wallace J, Elgendy H, Lieberman J, Laurencin C. Bone and Biomaterials. An Introduction to Biomaterials and their Applications. $2^{nd}$ edn., Taylor & Francis group/CRC Press (2011) pp. 571-593.
13. Burg K J, Porter S, Kellam J F. Biomaterial developments for bone tissue engineering. Biomaterials. 2000; 21(23):2347-59.
14. Petite H, Viateau V, Bensaïd W, Meunier A, de Pollak C, Bourguignon M, et al. Tissue-engineered bone regeneration. Nat Biotechnol. 2000; 18(9):959-63.
15. Reichert W M, Ratner B D, Anderson J, Coury A, Hoffman A S, Laurencin C T, et al. 2010 Panel on the Biomaterials Grand Challenges. J Biomed Mater Res A. 2010.
16. Hutmacher D W. Scaffolds in tissue engineering bone and cartilage. Biomaterials. 2000; 21(24):2529-43.

17. Albrektsson T, Johansson C. Osteoinduction, osteoconduction and osseointegration. Eur Spine J. 2001; 10 Suppl 2:S96-101.
18. Albrektsson T. The healing of autologous bone grafts after varying degrees of surgical trauma. A microscopic and histochemical study in the rabbit. J Bone Joint Surg Br. 1980; 62(3):403-10.
19. Vaccaro A R. The role of the osteoconductive scaffold in synthetic bone graft. Orthopedics. 2002; 25(5 Suppl): s571-8.
20. Karageorgiou V, Kaplan D. Porosity of 3D biomaterial scaffolds and osteogenesis. Biomaterials. 2005; 26(27): 5474-91.
21. Tsuruga E, Takita H, Itoh H, Wakisaka Y, Kuboki Y. Pore size of porous hydroxyapatite as the cell-substratum controls BMP-induced osteogenesis. J Biochem. 1997; 121 (2):317-24.
22. Kuboki Y, Jin Q, Takita H. Geometry of carriers controlling phenotypic expression in BMP-induced osteogenesis and chondrogenesis. J Bone Joint Surg Am. 2001; 83-A Suppl 1(Pt 2):S105-15.
23. Holtorf H L, Datta N, Jansen J A, Mikos A G. Scaffold mesh size affects the osteoblastic differentiation of seeded marrow stromal cells cultured in a flow perfusion bioreactor. J Biomed Mater Res A. 2005; 74(2):171-80.
24. Kühne J, Bartl R, Frisch B, Hammer C, Jansson V, Zimmer M. Bone formation in coralline hydroxyapatite. Effects of pore size studied in rabbits. Acta Orthop Scand. 1994; 65(3):246-52.
25. Volkmer E, Drosse I, Otto S, Stangelmayer A, Stengele M, Kallukalam B, et al. Hypoxia in static and dynamic 3D culture systems for tissue engineering of bone. Tissue Eng Part A. 2008; 14(8):1331-40.
26. Nam Y S, Yoon J J, Park T G. A novel fabrication method of macroporous biodegradable polymer scaffolds using gas foaming salt as a porogen additive. J Biomed Mater Res. 2000; 53(1):1-7.
27. Hou Q, Grijpma D W, Feijen J. Preparation of interconnected highly porous polymeric structures by a replication and freeze-drying process. J Biomed Mater Res B Appl Biomater. 2003; 67(2):732-40.
28. Yin Y, Ye F, Cui J, Zhang F, Li X, Yao K. Preparation and characterization of macroporous chitosan-gelatin/beta-tricalcium phosphate composite scaffolds for bone tissue engineering. J Biomed Mater Res A. 2003; 67(3):844-55.
29. Schugens C, Maquet V, Grandfils C, Jerome R, Teyssie P. Polylactide macroporous biodegradable implants for cell transplantation. II. Preparation of polylactide foams by liquid-liquid phase separation. J Biomed Mater Res. 1996; 30(4):449-61.
30. El-Ayoubi R, Degrandpré C, Diraddo R, Yousefi A M, Lavigne P. Design and Dynamic Culture of 3D-Scaffolds for Cartilage Tissue Engineering. J Biomater Appl. 2011; 25(5):429-44.
31. Kim H J, Kim U J, Leisk G G, Bayan C, Georgakoudi I, Kaplan D L. Bone regeneration on macroporous aqueous-derived silk 3-D scaffolds. Macromol Biosci. 2007; 7(5):643-55.
32. Kim H J, Kim U J, Vunjak-Novakovic G, Min B H, Kaplan D L. Influence of macroporous protein scaffolds on bone tissue engineering from bone marrow stem cells. Biomaterials. 2005; 26(21):4442-52.
33. Ma P X, Choi J W. Biodegradable polymer scaffolds with well-defined interconnected spherical pore network. Tissue Eng. 2001; 7(1):23-33.
34. Zhang J, Zhang H, Wu L, Ding J. Fabrication of three dimensional polymeric scaffolds with spherical pores J MATER SCI 2006; 41:1725-31
35. Wei G, Ma P X. Macroporous and nanofibrous polymer scaffolds and polymer/bone-like apatite composite scaffolds generated by sugar spheres. J Biomed Mater Res A. 2006; 78(2):306-15.
36. Mikos A G, Thorsen A J, Czerwonka L A, Bao Y, Langer R, Winslow D N, et al. PREPARATION AND CHARACTERIZATION OF POLY(L-LACTIC ACID) FOAMS. Polymer. 1994; 35(5):1068-77.
37. Martin I, Shastri V P, Padera R F, Yang J, Mackay A J, Langer R, et al. Selective differentiation of mammalian bone marrow stromal cells cultured on three-dimensional polymer foams. J Biomed Mater Res. 2001; 55(2):229-35.
38. Borden M, Attawia M, Khan Y, Laurencin C. Tissue engineered microsphere-based matrices for bone repair: design and evaluation. Biomaterials. 2002; 23(2):551-9.
39. Borden M, Attawia M, Khan Y, El-Amin S, Laurencin C. Tissue-engineered bone formation in vivo using a novel sintered polymeric microsphere matrix. J Bone Joint Surg Br. 2004; 86(8):1200-8.
40. Jiang T, Nukavarapu S, Deng M, Jabbarzadeh E, Kofron M, Doty S, et al. Chitosan-poly(lactide-co-glycolide) microsphere-based scaffolds for bone tissue engineering: In vitro degradation and in vivo bone regeneration studies. Acta Biomater. 2010.
41. Boschetti F, Tomei A A, Turri S, Swartz M A, Levi M. Design, fabrication, and characterization of a composite scaffold for bone tissue engineering. Int J Artif Organs. 2008; 31(8):697-707.
42. Nukavarapu S, Kumbar S, Brown J, Krogman N, Weikel A, Hindenlang M, et al. Polyphosphazene/nano-hydroxyapatite composite microsphere scaffolds for bone tissue engineering. Biomacromolecules. 2008; 9(7):1818-25.
43. Moore M J, Jabbari E, Ritman E L, Lu L, Currier B L, Windebank A J, et al. Quantitative analysis of interconnectivity of porous biodegradable scaffolds with micro-computed tomography. J Biomed Mater Res A. 2004; 71(2):258-67.
44. Moonen J R, Krenning G, Brinker M G, Koerts J A, van Luyn M J, Harmsen M C. Endothelial progenitor cells give rise to pro-angiogenic smooth muscle-like progeny. Cardiovasc Res. 2010; 86(3):506-15.
45. Deng M, Nair L S, Nukavarapu S P, Kumbar S G, Brown J L, Krogman N R, et al. Biomimetic, bioactive etheric polyphosphazene-poly(lactide-co-glycolide) blends for bone tissue engineering. Journal of Biomedical Materials Research Part A. 2010; 92A(1):114-25.
46. Viktorov I, Proshin S. Use of isopropyl alcohol in histological assays: dehydration of tissue, enbessing into paraffin, and processing of paraffin sections. Bull Exp Biol Med. 2003; 136(1):105-6.
47. Athanasiou K A, Zhu C, Lanctot D R, Agrawal C M, Wang X. Fundamentals of biomechanics in tissue engineering of bone. Tissue Eng. 2000; 6(4):361-81.
48. Hao W, Pang L, Jiang M, Lv R, Xiong Z, Hu Y Y. Skeletal repair in rabbits using a novel biomimetic composite based on adipose-derived stem cells encapsulated in collagen I gel with PLGA-beta-TCP scaffold. J Orthop Res. 2010; 28(2):252-7.
49. Yu H, Matthew H W, Wooley P H, Yang S Y. Effect of porosity and pore size on microstructures and mechanical properties of poly-epsilon-caprolactonehydroxyapatite composites. J Biomed Mater Res B Appl Biomater. 2008; 86B(2):541-7.

50. Han D, Zhang Q. An essential requirement for osteoclasts in refined bonelike tissue reconstruction in vitro. Med Hypotheses. 2006; 67(1):75-8.
51. Feng B, Jinkang Z, Zhen W, Jianxi L, Jiang C, Jian L, et al. The effect of pore size on tissue ingrowth and neovascularization in porous bioceramics of controlled architecture in vivo. Biomed Mater. 2011; 6(1):015007.
52. Amini A, Wallace J, Nukavarapu S. Short-term and Long-term Effects of Orthopaedic Biodegradable Implants Journal of Long-Term Effects of Medical Implants. J Long Term Eff Med Implants. 2011; 21(2): 93-122.
53. El-Ayoubi R, Eliopoulos N, Diraddo R, Galipeau J, Yousefi A M. Design and fabrication of 3D porous scaffolds to facilitate cell-based gene therapy. Tissue Eng Part A. 2008; 14(6):1037-48.
54. Murphy C, O'Brien F. Understanding the effect of mean pore size on cell activity in collagen-glycosaminoglycan scaffolds. Cell Adh Migr. 2010; 4(3).
55. Klenke F M, Liu Y, Yuan H, Hunziker E B, Siebenrock K A, Hofstetter W. Impact of pore size on the vascularization and osseointegration of ceramic bone substitutes in vivo. J Biomed Mater Res A. 2008; 85(3):777-86.
56. Druecke D, Langer S, Lamme E, Pieper J, Ugarkovic M, Steinau H U, et al. Neovascularization of poly(ether ester) block-copolymer scaffolds in vivo: longterm investigations using intravital fluorescent microscopy. J Biomed Mater Res A. 2004; 68(1):10-8.
57. Yaszemski M J, Payne R G, Hayes W C, Langer R, Mikos A G. Evolution of bone transplantation: molecular, cellular and tissue strategies to engineer human bone. Biomaterials. 1996; 17(2):175-85.
58. Lv Q, Nair L, Laurencin C T. Fabrication, characterization, and in vitro evaluation of poly(lactic acid glycolic acid)/nano-hydroxyapatite composite microsphere-based scaffolds for bone tissue engineering in rotating bioreactors. J Biomed Mater Res A. 2009; 91(3):679-91.
59. Aydin H M, El Haj A J, Piskin E, Yang Y. Improving pore interconnectivity in polymeric scaffolds for tissue engineering. J Tissue Eng Regen Med. 2009; 3(6):470-6.
60. Yu X, Botchwey E A, Levine E M, Pollack S R, Laurencin C T. Bioreactorbased bone tissue engineering: the influence of dynamic flow on osteoblast phenotypic expression and matrix mineralization. Proc Natl Acad Sci USA. 2004; 101(31):11203-8.
61. Stevens B, Yang Y, Mohandas A, Stucker B, Nguyen K T. A review of materials, fabrication methods, and strategies used to enhance bone regeneration in engineered bone tissues. J Biomed Mater Res B Appl Biomater. 2008; 85(2):573-82.
62. Abousleiman R I, Sikavitsas V I. Bioreactors for tissues of the musculoskeletal system. Adv Exp Med Biol. 2006; 585:243-59.
63. Eiselt P, Kim B S, Chacko B, Isenberg B, Peters M C, Greene K G, et al. Development of technologies aiding large-tissue engineering. Biotechnol Prog. 1998; 14(1): 134-40.
64. Granet C, Laroche N, Vico L, Alexandre C, Lafage-Proust M H. Rotatingwall vessels, promising bioreactors for osteoblastic cell culture: comparison with other 3D conditions. Med Biol Eng Comput. 1998; 36(4):513-9.
65. Li C, Vepari C, Jin H J, Kim H J, Kaplan D L. Electrospun silk-BMP-2 scaffolds for bone tissue engineering. Biomaterials. 2006; 27(16):3115-24.
66. Laurencin C T, Attawia Mass., Lu L Q, Borden M D, Lu H H, Gorum W J, et al. Poly(lactide-co-glycolide)/hydroxyapatite delivery of BMP-2-producing cells: a regional gene therapy approach to bone regeneration. Biomaterials. 2001; 22(11):1271-7.
67. Simmons C A, Alsberg E, Hsiong S, Kim W J, Mooney D J. Dual growth factor delivery and controlled scaffold degradation enhance in vivo bone formation by transplanted bone marrow stromal cells. Bone. 2004; 35(2): 562-9.
68. Peng H, Wright V, Usas A, Gearhart B, Shen H C, Cummins J, et al. Synergistic enhancement of bone formation and healing by stem cell-expressed VEGF and bone morphogenetic protein-4. J Clin Invest. 2002; 110 (6):751-9.

Example 2. Design, Fabrication and In Vitro Evaluation of Novel Polymer-Hydrogel Osteoinductive Scaffold for Bone Tissue Engineering The development of a bone mechanically-compatible and osteoinductive scaffold is important for bone tissue engineering applications, particularly for large area/critically sized bone defect repair and regeneration. Although previous studies with weight-bearing scaffolds have shown promising results, there is a clear need to develop better osteoinductive strategies for effective scaffold-based bone regeneration. In this study, we designed and fabricated a novel polymer hydrogel hybrid scaffold system in which a load-bearing polymer matrix and a peptide hydrogel allow for the synergistic combination of mechanical strength and osteoinductivity in a single scaffold. The hybrid scaffold system promoted increased pre-osteoblastic cell proliferation. Further, we biotinylated human recombinant bone morphogenetic protein 2 (rhBMP2), and characterized the biotin addition and its effect on rhBMP2 biological activity. The biotinylated rhBMP2 was tethered to the hybrid scaffold using biotin-streptavidin complexation. Controlled release studies demonstrated increased rhBMP2 retention with the tethered rhBMP2 hybrid scaffold group. In vitro evaluation of the hybrid scaffold was performed with rat bone marrow stromal cells and mouse pre-osteoblast cell line MC3T3-E1 cells. Gene expression of alkaline phosphatase (ALP) and osteocalcin (OC) increased in both cell types seeded on the rhBMP2 tethered hybrid scaffolds over the untethered counterparts, demonstrating osteoinductive potential of our hybrid graft. These findings demonstrate the suitability of the novel "polymerhydrogel" hybrid system as a weight-bearing and osteoinductive scaffold for effective bone tissue engineering.

The aim of the present study was to develop a biodegradable hybrid scaffold system that is weight-bearing and osteoinductive for effective bone regeneration. A hybrid scaffold system was developed by combining 3D porous poly(85lactide-co-15glycolide) (PLGA)/nanohydroxyapatite (nHA) matrices with (Arginine-Alanine-Aspartic Acid-Alanine)$_4$ (RADA-16) self-assembling peptide hydrogel. The gel matrix was modified to allow for covalent binding with osteoinductive factor, BMP2. In this paper, we report hybrid graft design, fabrication, and the scaffold osteoinductivity characterization in vitro.

Materials and Methods

Microsphere Fabrication

Poly(85 lactide-co-15 glycolide)/nano-hydroxyapatite (PLGA/nHA) composite microspheres were prepared by an oil-in-water emulsion method as reported previously (Nukavarapu et al. 2008). In brief, PLGA 85/15 (Lakeshore Biomaterials, Birmingham, Ala., USA) and nHA(Advanced Biomaterials Inc., Berkeley, Calif., USA) were mixed at a ratio of 4 g of PLGA to 1 gram of nHA and dissolved in methylene chloride (L-14119, Fisher Scientific, Pittsburgh, Pa.) in a 1:5 dilution ratio (i.e., 4 g PLGA:20 milliliters of methylene chloride). The PLGA/nHA in methylene chloride solution was slowly poured into 1 liter of 1% polyvinyl alcohol (Sigma-Aldrich, St. Louis, Mo.) solution under a stirring speed of 250 RPM. The stirring continued for 24 hours to allow methylene chloride to evaporate. The resultant composite microspheres were washed with distilled water, filtered, air-dried, and sieved into different sizes.

Macro-Porous Scaffold Fabrication

Macro-porous matrices with interconnected porosity were fabricated via a "thermal sintering and porogen leaching" technique described in Example 1. In brief, PLGA/nHA composite microspheres (in the size range 425-600 um) were mixed with a porogen, NaCl (diameter 200-300 um) at ratios of 75:25 and packed into a steel mold designed to produce circular discs of 10 mm diameter and 2 mm thickness. The mold was placed in an oven and thermally sintered at 106° C. for 1 hour. After the sintering, the porogen was leached out by soaking the microsphere-NaCl matrix in distilled water for 30 minute and then washed twice in distilled water. The resulting scaffolds were dried and stored in a desiccator until further use.

Rat Bone Marrow Stromal Cell Isolation and Culture

Rats 6- to 8-week-old (n=4) were sacrificed by $CO_2$ asphyxiation. The femurs and tibias were aseptically dissected out, cleaned and washed with sterile PBS under the hood. The epiphyseal growth plates were removed and bone marrow cells were flushed out using 18-G needle attached to a 10 ml syringe. The bone marrow flush in 10 ml of α-MEM (Invitrogen, Grand Island, N.Y., USA) culture media containing 100 U/ml penicillin, 100 μg/ml streptomycin and 10% fetal calf serum (HyClone, Logan, Utah, USA) were passed through a 70-μm cell strainer (Fisher Scientific, Pittsburgh, Pa., USA). The resulting cell suspension was carefully layered on top of 10 ml of Lymphoprep™ (Axis-Shield PoC AS, Oslo, Norway) in a 50 ml falcon tube and then centrifuged at 600 g for 30 minute. The mononuclear cell fraction was collected, washed with 3 volumes of PBS then plated in a T75 flask. After 2-3 days of culture, adherent cells representing the bone marrow stromal cell population were trypsinized and cultured until passage 4 before freezing them in liquid nitrogen.

Hybrid Scaffold Fabrication

Self-assembling peptide gel solution, (Arginine-Alanine-Aspartic Acid-Alanine)$_4$ (RADA-16) (Puramatrix™, BD biosciences, Franklin Lakes, N.J., USA) was prepared as directed by the manufacturer and then infused into the PLGA/nHA macro-porous matrices. The resulting integrated scaffolds were placed in a 24 well plate; media was added to induce hydrogel formation. These hydrogel infused matrices are referred to as "polymer-hydrogel" hybrid scaffolds. Prior to gel infusion into the PLGA microsphere scaffolds, the gel solution was mixed with MC3T3-E1 or primary rat stromal cells in 10% sucrose solution (with 1:1 or 1:2 ratios) to form cellularized hybrid scaffolds. Cells were encapsulated at density of 100,000 cells/scaffold. After 1 hour media was replaced with fresh media. The hybrid scaffolds, both with or without cells were further cultured for 14 days. Ponceau S staining was used to evaluate hydrogel infusion, and live-dead staining was utilized to study cell viability.

Live-Dead Assay and Confocal Microscopy

Live-dead cell viability assay (Invitrogen, Carlsbad, Calif., USA) was used to monitor cell survival and growth in hybrid scaffolds. The scaffolds were taken out of the culture at pre-determined time points, days 1, 7 and 14, and stained for live-dead cells. The assay was performed according to the manufacturer's instructions, and the hybrid grafts with stained cells were visualized using Zeiss 510 laser scanning confocal microscopy (Carl Zeiss Microlmaging, LLC, Thornwood, N.Y., USA) where live cells stained green and dead cells stained red.

Analysis of Cell Proliferation on Hybrid Scaffold

Cell proliferation was evaluated quantitatively on nHA/PLGA control and hybrid scaffolds using Quant-iT™ PicoGreen™ dsDNA assay (Invitrogen, Carlsbad, Calif., USA). After culturing the samples for 1, 7, and 14 days in basal media, the cell-scaffold samples (n=4) for each experimental group were harvested. Samples were washed with PBS, incubated in lysis buffer (0.5% Triton X-100, 1 mM mgcl2, 10 mM Tris-HCL), and subjected to freeze-thaw cycles. DNA concentration from the cell lysates was determined according to the manufacturer's protocol.

BMP2 Biotinylation

Biotinylation of human recombinant bone morphogenetic factor-2 (rhBMP2, Piscataway, N.J., USA) was achieved using biotinylation kit from Solulink (San Diego, Calif., USA). rhBMP2 30-50 ug in 20 mM acetic acid PBS was ion exchanged into protein modification buffer. Biotin conjugated with PEG spacer and chromogen that excites at 340 nm was reacted with rhBMP2 for 30 min. Biotinylated rhBMP2 was tested for the presence of biotin using western blot and surface Plasmon resonance with BIACORE™ instrument. The bioactivity of biotin-BMP2 was compared with unmodified BMP2 using MC3T3-E1 and rat BMSCs cells. Biotin conjugated SAP was synthesized by Bachem Americas (Torrance, Calif., USA), peptide synthesis was verified by amino acid sequencing.

Western Blotting

Five hundred nanograms of modified rhBMP2 was separated on a 12% sodium dodecyl sulfate polyacrylamide gel electrophoresis (SDS-PAGE) gel as previously described (Andrassy et al. 2006), followed by electroblotting to an ECL-nitrocellulose membrane. Membranes were blocked overnight in 5% non-fat milk, and then incubated with primary antibody against BMP2 (R&D Systems, Inc., Minneapolis, Minn., USA) at a concentration of 1:1,000 for 60 minutes at room temperature. After washing (2×7 minutes in Tris-buffered saline, 0.05% Tween), the secondary antibody (horseradish peroxidase-coupled rabbit IgG, 1:3000) was added, and incubation was continued for 45 minutes at room temperature. Membranes were washed three times for 5 minutes as above followed by a final 5-minute wash in Tris-buffered saline. Immunoreactive proteins were detected with the ECL-Western blot system and subsequent autoradiography for 2 to 10 minutes.

Biotin Conjugation Analysis

Biotin conjugation with SAP and BMP2 protein was evaluated using Biacore T100 optical biosensor (GE Healthcare, Pittsburgh, Pa., USA) by adopting a standard procedure (Sachse et al. 2005), (Balasubramanian et al. 2010). Streptavidin was covalently immobilized on a CM5 sensor chip (Biacore, Uppsala, Sweden). The amount of protein immobilized on the chip was 5000 resonance units (RU), corresponding to 5 ng/mm2. Biotinylated SAP or BMP2 in HSB buffer (10 mM HEPES of pH 7.4 containing 3 mM EDTA, 0.15 M NaCl, and 0.05% surfactant P20) were injected over the sensor surface at a flow rate of 30 μl/min for 180 s followed by HSB buffer without analyte. The surface was regenerated between injections by using 10 mM NaOH at a flow rate of 50 μl/min for 30 s. Unmodified SAP or rhBMP2 served as a control. The recorded sensorgrams were analyzed using the Biacore T100 evaluation software.

BMP2 Biological Activity

Primary rat stromal cells or MC3T3-E1 pre-osteoblastic cells were cultured in the presence of BMP2 or biotin-BMP2 at a concentration of 100 ng/ml in mineralization media containing 50 ug/ml ascorbic acid and 5 mM beta-glycerol phosphate. Alkaline phosphatase and von Kossa staining was performed at day 14 for MC3T3 cells and for rat BMSCs. ALP activity was performed using a commercially available kit (86-R ALP; Sigma Diagnostics, Inc., Mo., USA) according to the manufacturer's instruction and as used previously (Igwe et al. 2011). Briefly cells were fixed in acetone/glutaraldehyde citrate buffered solution for 2 minutes, rinsed in distilled water and incubated with ALP substrate solution for 30 minutes. After washing with distilled water, and air dried overnight, von Kossa staining was performed by incubation with 5% silver nitrate solution and subsequent exposure to UV light. After removing silver nitrate solution, the plates were washed with distilled water and air dried overnight. Images were acquired using a microscope equipped with digital camera.

BMP2 Release Kinetics

To obtain biotinylated hydrogel, Puramatrix™ solution (self-assembled RADA-16 gel) was mixed with biotin conjugated RADA-16 peptide at a ratio of 10:1. BMP2 biotin was tethered to streptavidin via biotin-streptavidin complexation. For the complexation, BMP2 biotin, streptavidin were mixed at a ratio of 1:2.3. Aliquots of 2 ug of BMP2-biotin complexed with streptavidin, and 100 ul of 0.5% self-assembling peptide gel with biotin were mixed to form gel in 96 well plate by adding 150 ul serum free α-MEM media containing 0.05% sodium azide. 100 ul media was collected and the same volume was replaced at 1, 4, 7 and 14 days. The amount of BMP2 present in the collected media was assayed using ELISA (R&D Systems, Inc., Minneapolis, Minn.) according to the manufacturer's protocol RNA Isolation and Gene Expression Analysis Primary rat stromal cells or MC3T3-E1 pre-osteoblastic cells were resuspended in 0.5% self-assembling peptide alone or with 500 ng/ml BMP2 untethered/with 500 ng/ml tethered BMP2. Subsequently, the gel solution containing cells were infused into PLGA/nHA macro-porous scaffold at a density of 105 cells/scaffold and then cultured for 7 and 14 days in osteogenic media. At days 7, and 14, cells were harvested and total RNA was extracted using Qiagen RNA isolation kit. Scaffolds were rinsed in PBS, and then transferred into 1.5 ml eppendorf tubes containing RNA lysis buffer placed on ice. Scaffolds were broken into pieces and vortexed repeatedly for 1 min, the resulting solution was passed through an RNA shredder column and subsequently used for RNA isolation. After RNA isolation, 1-2 ug of total RNA was reverse transcribed into cDNA using Invitrogen cDNA synthesis kit (Carlsberg, Calif., USA). Semi-quantitative real-time PCR was carried out using the TaqMan™ gene expression assays, the mouse primers (ALP: Mm01187117_ml, GAPDH: Mm99999915_gl, OC: Mm03413826 mH) and Rat primers (ALP: Rn01516028_ml, GAPDH: Rn01775763_gl, OC: Rn01455285 gl) were from (Applied Biosystems, Calif., USA).

Statistical Analysis

To compare differences in mean, we used student t-test. $P<0.05$ was considered statistically significant.

Results

"Polymer-Hydrogel" Hybrid Graft Formation

Figure 12:
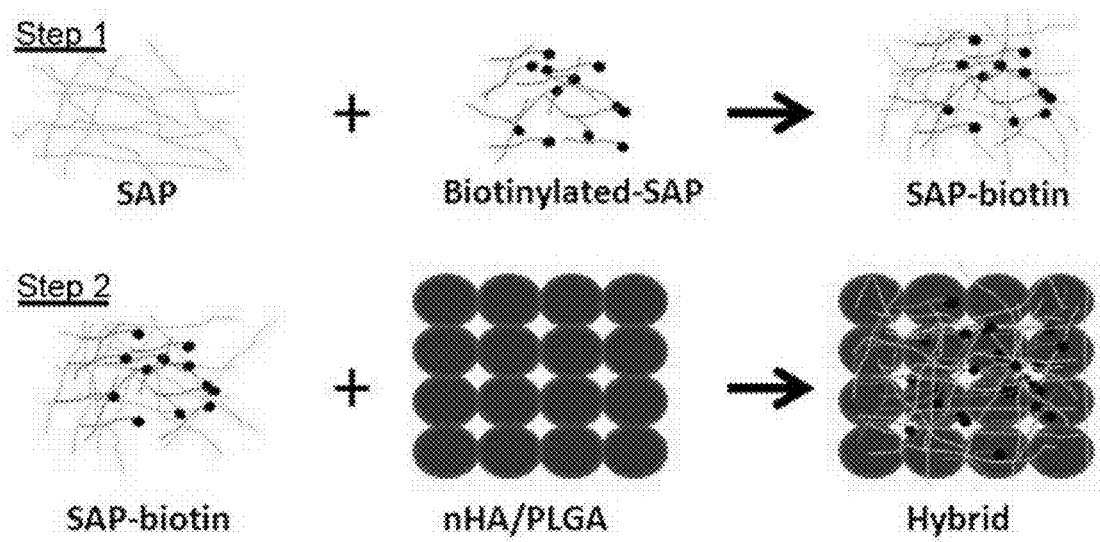
FIG. 12. Schematic representation of steps and methods used to generate "polymer-hydrogel" hybrid scaffold. Step 1 involves combining unmodified self-assembling peptide (SAP) with biotin-SAP at a ratio of 9:1 to generate biotinylated SAP gel. In the second step, biotinylated SAP and biotinylated BMP2 are linked with streptavidin, mixed with cells and then infused into prefabricated porous nHA/PLGA scaffolds to fabricate "SAP hydrogel-PLGA matrix" hybrid scaffold.
Figure 13:
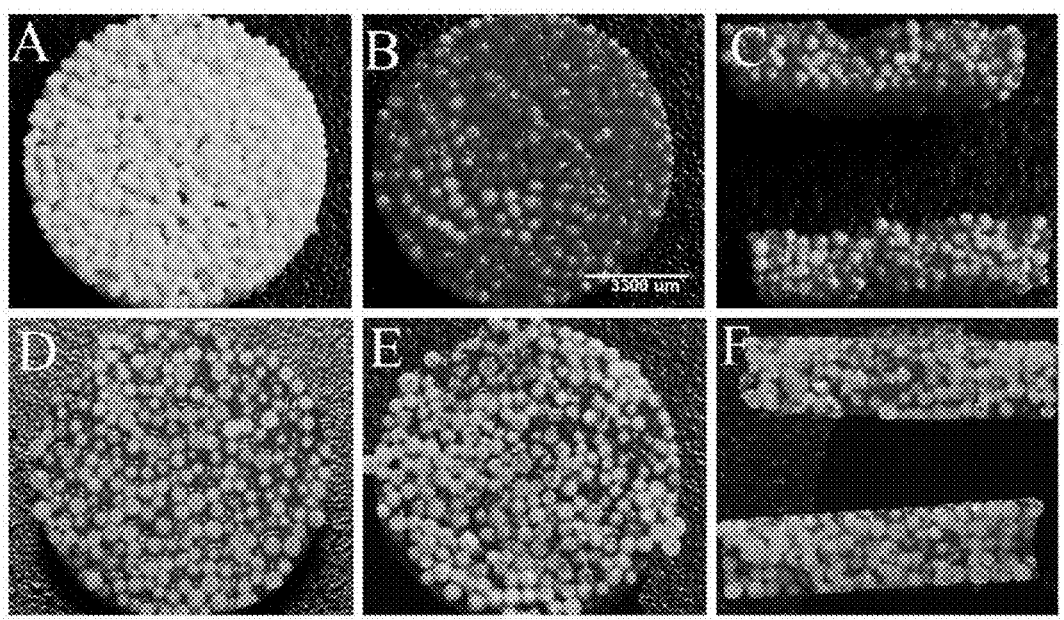
FIG. 13. Hybrid scaffold visualized via Ponceau S red staining. The Ponceau S red selectively stains SAP gel phase of the "SAP gel-nHA/PLGA matrix" hybrid scaffold. Photographic images are shown for (a) nHA/PLGA matrix alone, and (b-f) SAP gel infused nHA/PLGA hybrid scaffolds. Images B, D, and E show staining on hybrid scaffolds cultured for 1 hour, 7 days, and 14 days, respectively. Cross-sectional staining after 1 hour and 14 days of culture are shown in (C) and (F), respectively.

Hybrid scaffold was generated by infusing nHA/PLGA microsphere scaffolds with SAP hydrogel. FIG. 12 presents the steps employed in generating the hybrid scaffold. As shown in the scheme, SAP hydrogel was chemically modified to generate SAP-biotin to allow for tethering of biotinylated growth factors. Furthermore, the hybrid scaffold formation was visualized by Ponceau S staining. As shown in FIG. 13, the Ponceau S red stained the SAP hydrogel infused in nHA/PLGA microsphere scaffold. Uniform infusion was observed throughout the scaffold (FIG. 13A-C). In addition, the Ponceau S red stain intensity was observed to decrease with culture time (FIG. 13). These results show that SAP hydrogel can be formed within the pores of a 3D-scaffold to fabricate a "polymer-hydrogel" integrated scaffold system for bone tissue engineering applications.

Hybrid Scaffolds: Cell Viability and Proliferation

Figure 14:
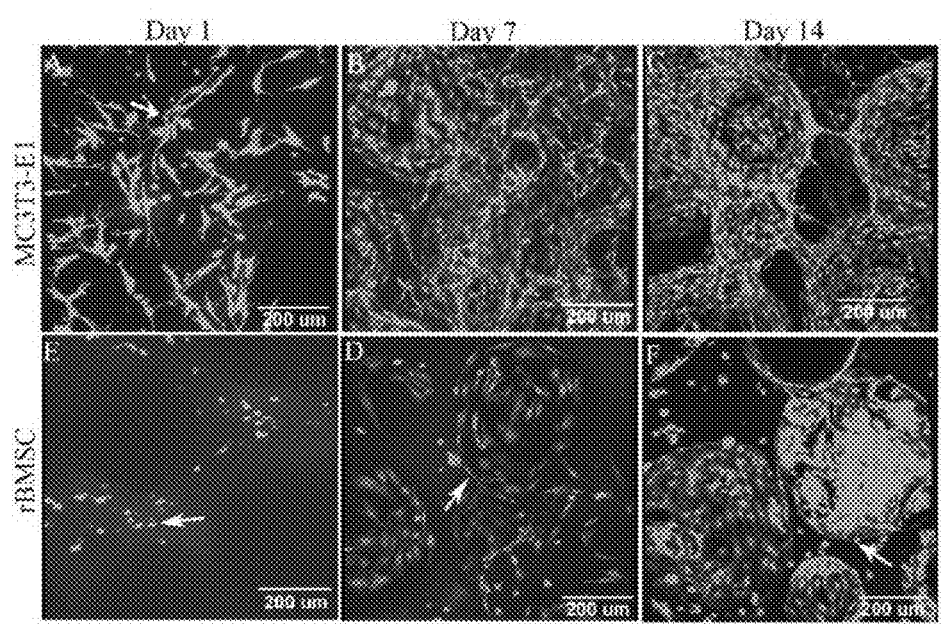
FIG. 14. Growth and survival of MC3T3-E1 and rBMSC cells in hybrid scaffold. Images show live and dead cells cultured on hybrid scaffolds. (A-C) show confocal images recorded on the scaffolds with MCET3-E1 cells, and (DF) show images on the scaffolds with rBMSC. The scanning depth is 200-250 um with a layer thickness in the range of 2.5-1.5 um. Arrows indicate cells, the images are recorded at 10× magnification.
Figure 15:
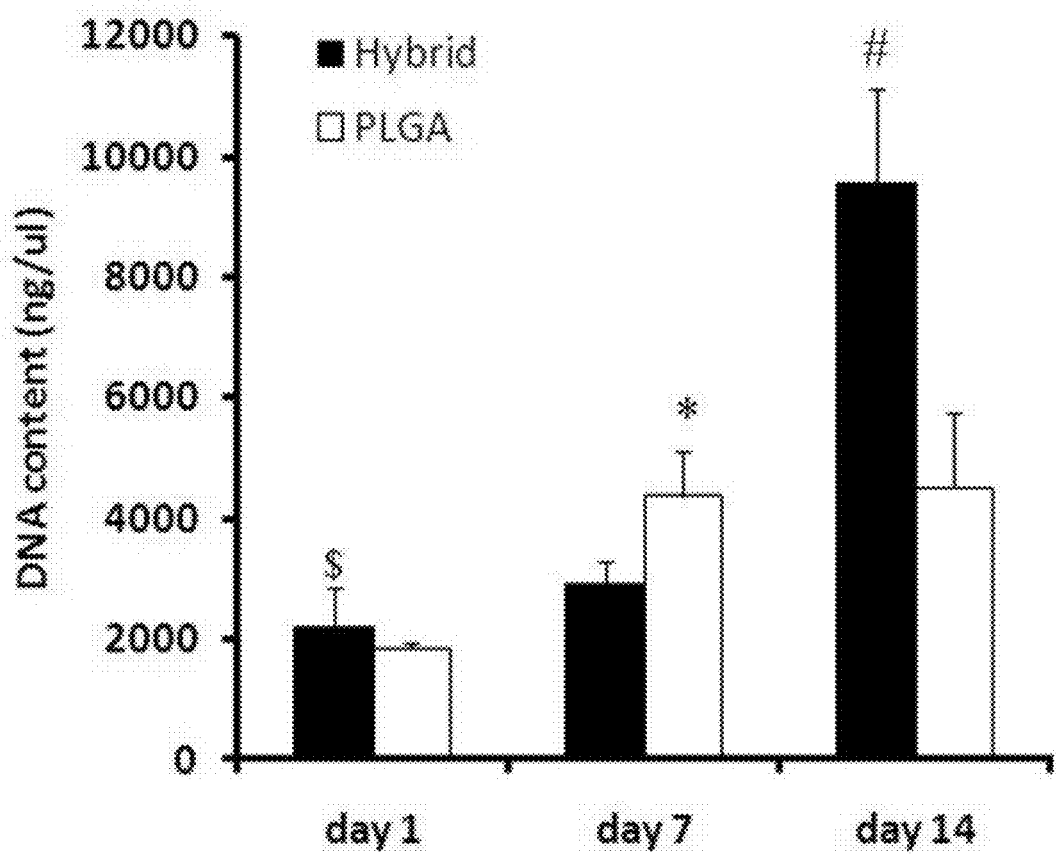
FIG. 15. rBMSC cell proliferation in nHA/PLGA and "nHA/PLGA-RADA hydrogel" hybrid scaffold. Results of picogreen assay showing DNA content of rBMSCs cultured for 1, 7, and 14 days. \$=significant compared to day 1 PLGA, * is significant compared to PLGA day 1 & hybrid day 7, # is significant over all groups (n=4, p<0.05).

To assess the osteoconductivity of the hybrid scaffold, cell viability and proliferation of rBMSCs and MC3T3-E1 pre-osteoblast cells cultured on the fabricated hybrid scaffold was evaluated. As shown in FIG. 14, significant growth and survival of both MC3T3-E1 pre-osteoblasts and the rBMSCs were observed in the hybrid scaffold. Assessment of cell viability using live-dead staining and laser scanning microscopy demonstrated that 24 hours (FIGS. 3A & D) after cells were seeded on the hybrid scaffold, cells were localized at the inter-microsphere spaces supported by the hydrogel. Furthermore, by day 7 (D7) (FIGS. 14B & E), cells began migrating towards the surfaces of the nHA/PLGA microsphere scaffold, and by day 14 (FIGS. 14C & F), the hybrid scaffold became fully cellularized. In addition, DNA picogreen assay was used to measure growth and proliferation of rBMSCs cultured on the hybrid scaffolds. High cell seeding efficiency was observed after 24 hours for cells grown on hybrid scaffold compared to control PLGA scaffolds (FIG. 15). For control nHA/PLGA scaffolds, DNA content progressively increased from day 1 to day 7 (n=4, p<0.05), but plateaued by day 14, whereas in hybrid scaffold, DNA content was significantly different between day 1 and 7, and between day 7 and 14 (n=4, p<0.05). Taken together, these results demonstrate that PLGA/nHA composite combined with self-assembly peptide supports growth and survival of both osteoprogenitor and pre-osteoblast cell.

Biotinylated rhBMP2 and SAP

Figure 16:
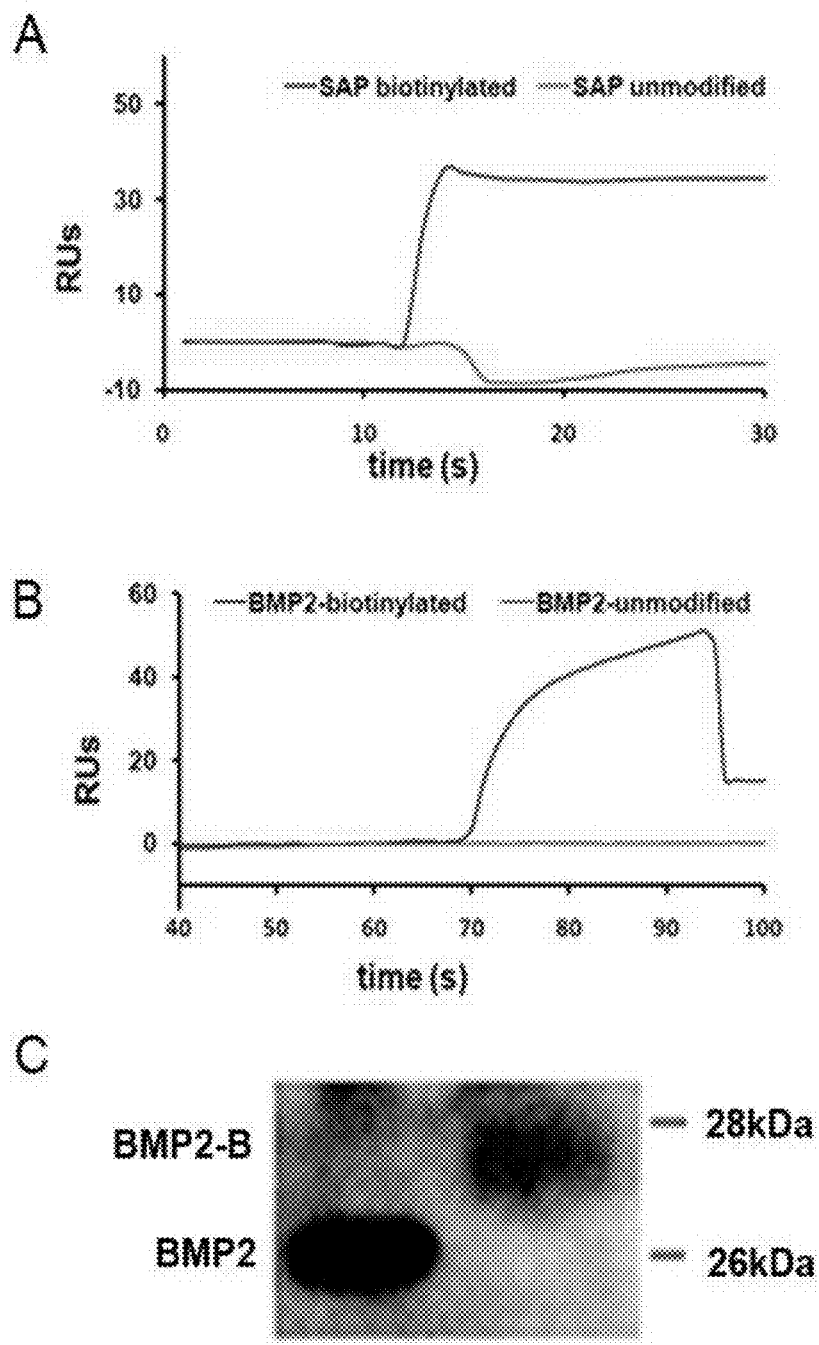
FIG. 16. Detection of biotin conjugated to SAP and BMP2. BIACORE measurement of biotin-streptavidin binding: (A-B) shows sensogram of SAP biotin (A) and BMP2 biotin (B). Plots show sensograms recorded for biotinylated and non-biotinylated groups, respectively. (C) Shows BMP2 Western blot with 500 ng protein, Lane 1=BMP2 unmodified, lane 2=biotinylated BMP.

To achieve biotin incorporation into the self-assembling peptide hydrogel, RADA-16, a custom synthesized biotinylated self-assembling peptide was procured. The peptide was designed such that its amino-acid sequence is similar to Puramatrix™, and moreover has a spacer between the biotin and SAP fragment in order for the biotin to be available for binding with streptavidin. Recombinant hBMP2 was chemically modified by biotin conjugated to a water-soluble sulfosuccinimidyl ester functional group which modifies protein lysine residues in an aqueous buffer. Optimal biotinylation of rhBMP2, corresponding to 0.7-0.9 molar substitution ratio (MSR) was achieved when the biotinylation reaction was limited to 30 minutes. Biotinylation of rhBMP2 and SAP was verified by recording biacore sensograms of molecular association and dissociation. Injection of SAP biotin over streptavidin modified CM5 chips demonstrated a peak characteristic of streptavidin-biotin binding (FIG. 16A), (Sachse et al. 2005). Similarly, biotinylated rhBMP2 exhibited streptavidin-biotin binding unlike the unmodified rhBMP2 (FIG. 16B). In addition, Western blot analysis of rhBMP2 and biotinylated rhBMP2 (FIG. 5C) showed a shift in the molecular weight of rhBMP2 from 26 to 27 kDa indicating biotin conjugation with rhBMP2. Taken together, these results confirm biotin conjugation with SAPs and rhBMP2. It is important to achieve biotin conjugated rhBMP2 and SAP fragments, because our study aims to utilize biotin-streptavidin complexation method for covalently binding rhBMP2 to SAP gel.

Biological Activity of Biotinylated rhBMP2

Figure 17:
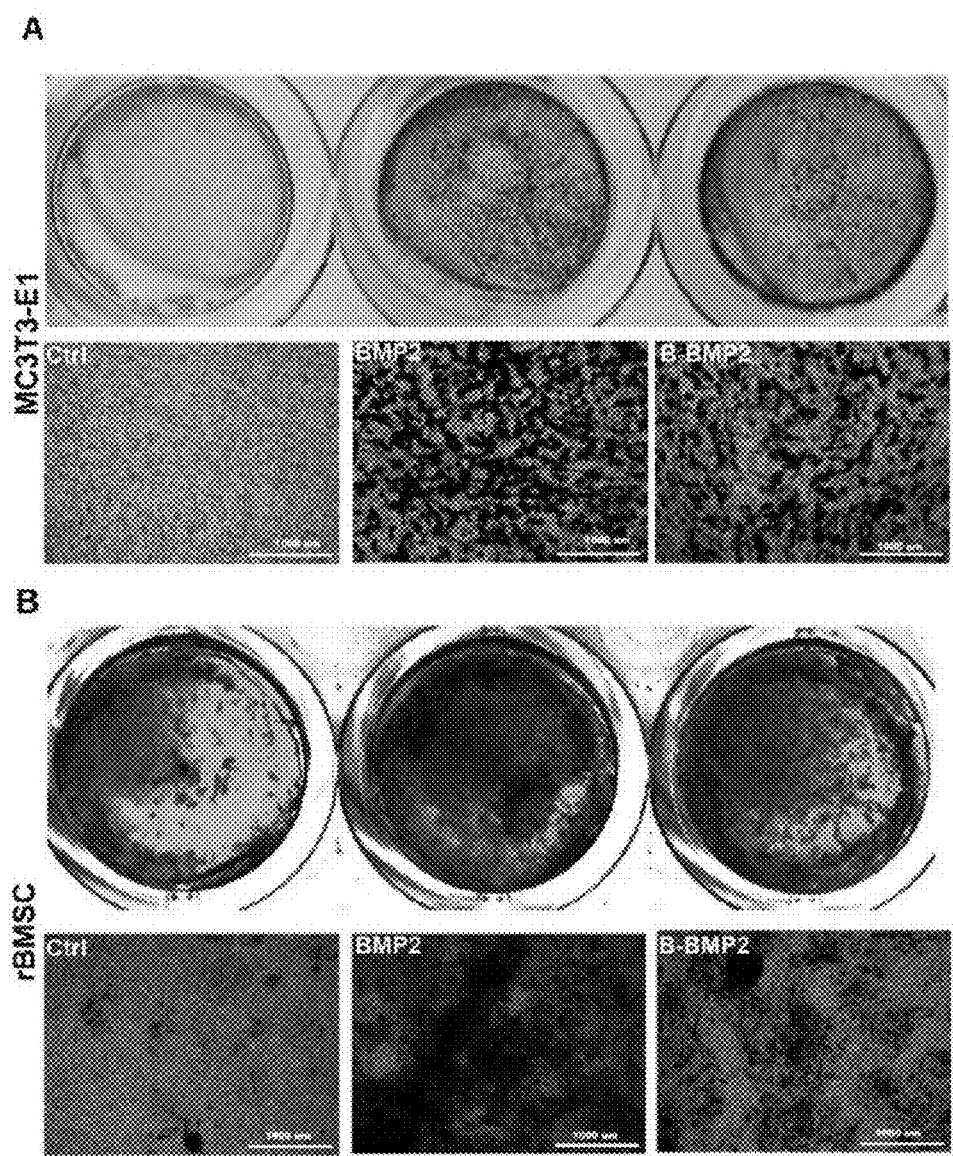
FIG. 17. Biological activity of biotinylated BMP2 with (A) MC3T3-E1 preosteoblasts, and (B) rBMSCs.; panels show microscopic and scanned images of alkaline phosphatase activity/von Kossa staining in cultures grown in mineralization media, mineralization media plus 100 ng/ml of either BMP2, or biotinylated BMP2 (B-BMP2).

Chemical modification of proteins and peptides can result in loss of biological activity. To exclude this possibility, biological activity of biotinylated rhBMP2 was investigated in vitro using MC3T3-E1 and bone marrow stromal cells (rBMSCs). MC3T3 cells are pre-osteoblast cell line with basal alkaline phosphatase expression, but with the potential to secrete and deposit minerals when cultured in osteogenic media (mineralization media supplemented with BMP2). BMSCs are known to differentiate towards multiple lineages including the osteoblasts. MC3T3 cells, rBMSCs were cultured for 14 days in the presence of mineralization media (MM), and MM supplemented with biotinylated rhBMP2/ unmodified rhBMP2. The ALP activity of the cultures were determined using ALP kit from sigma and co-stained for mineral formation (von-Kossa staining), black regions shows mineral deposition. Detection of mineral deposit is an indication of terminally differentiated osteoblast phenotype. As shown in FIG. 17, both the biotinylated and non-biotinylated rhBMP2 groups demonstrated comparable alkaline phosphatase activity. Unmodified BMP2 displayed slightly higher mineralization compared to the biotinylated group, (FIG. 17). These findings are similar for MC3T3 and rat stromal cells.

In Vitro Release Profile of Biotin Modified rhBMP2

Figure 18:
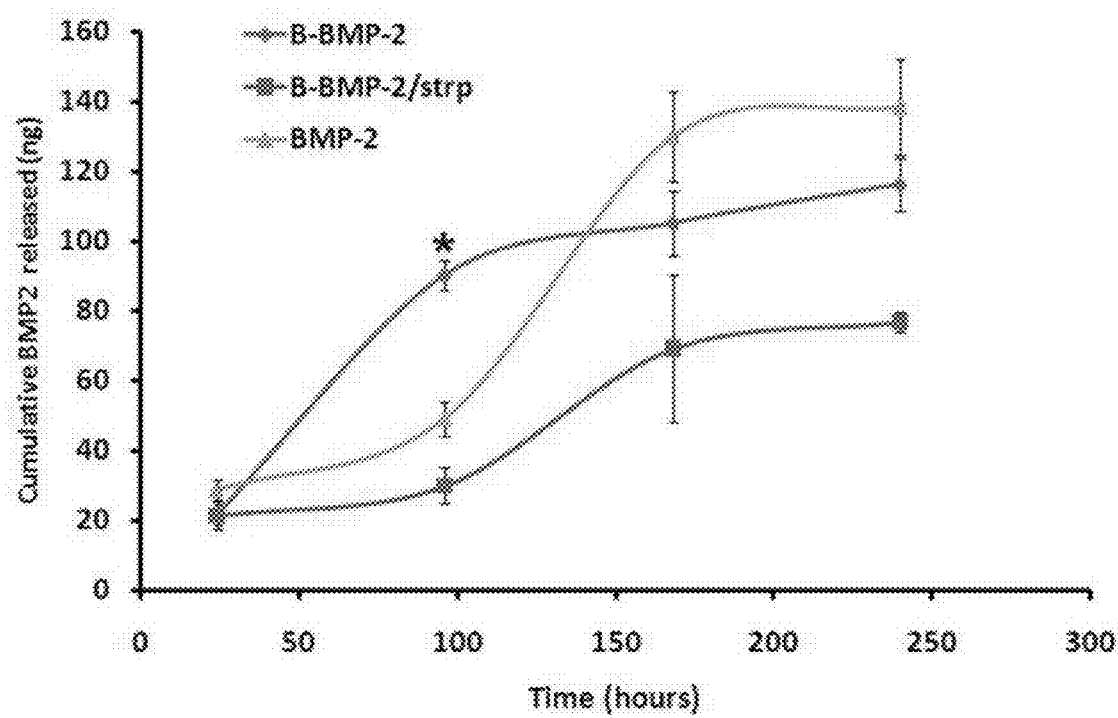
FIG. 18. In vitro release kinetics of biotinylated BMP2. Amount of BMP2 released over time was measured by ELISA. Results show cumulative release of rhBMP2 for un-tethered groups (BMP2-biotin, BMP2) versus tethered group (p<0.05, n=3).

A biotin-streptavidin sandwich method was utilized to conjugate rhBMP2 to self-assembled peptide nanofibers. Since each streptavidin molecule present four binding sites, in principle, it is possible to conjugate two SAP-biotins and two BMP2-biotins through a single streptavidin entity. The conjugated biotin-BMP2 is expected to become free in a controlled manner based on the SAP hydrogel degradation. In order to investigate rhBMP2 release kinetics, the amount of growth factor released was measured at 1, 3, 7, and 10 days, using ELISA. FIG. 18 shows the calculated cumulative release of BMP2 for the biotinylated SAP hydrogel groups loaded with BMP2-biotin, BMP2-biotin-streptavidin, and BMP2. The plots indicate that the cumulative release of rhBMP2 was significantly higher for the un-tethered groups (BMP2-biotin, BMP2) compared to the rhBMP2 tethered group throughout the duration of the release experiment. The observed trend suggest that tethering rhBMP2 via streptavidin-biotin resulted in a prolonged release of rhBMP2.

Effect of Tethered BMP2 on Osteogenic Differentiation of MC3T3-E1 and rBMSCs

Figure 19:
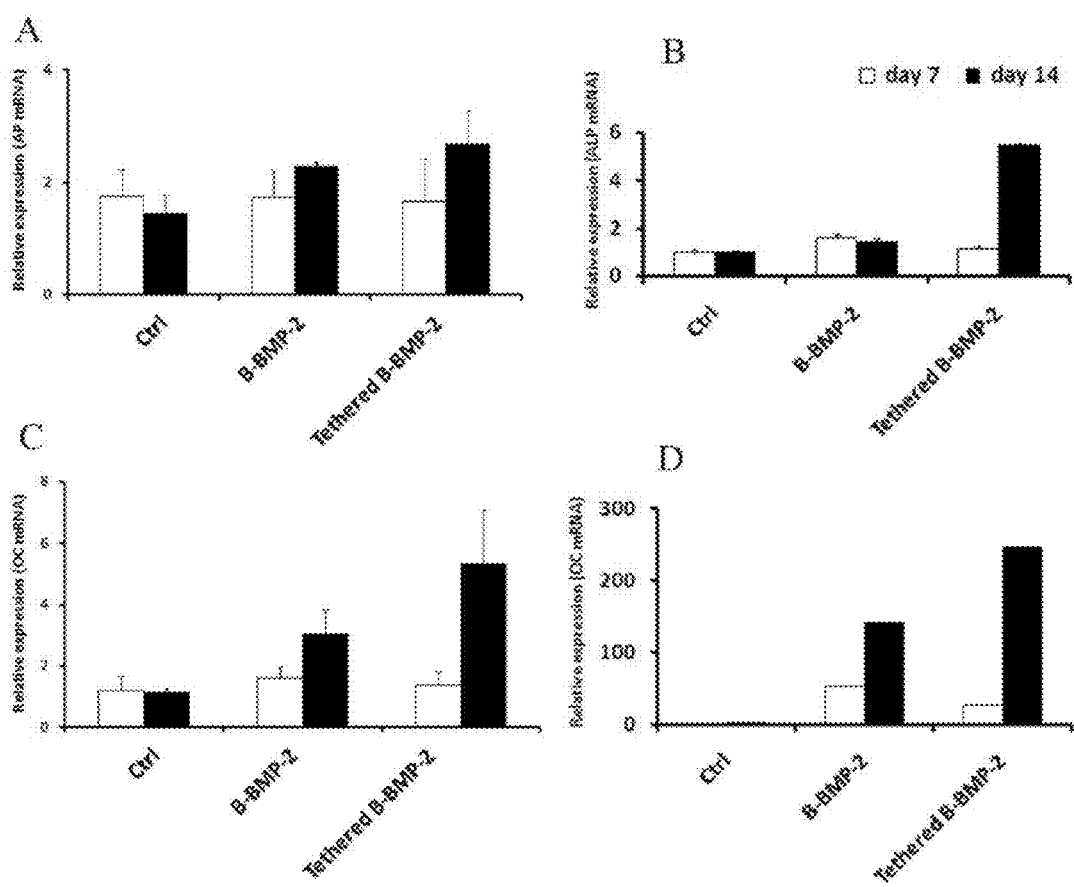
FIG. 19. Gene expression profile of cells grown in BMP2 untethered versus tethered SAP gelnHA/PLGA hybrid scaffolds. Panels show mRNA levels detected by qPCR for alkaline phosphatase expression in (A) MC3T3-E1 cells, (B) rBMSC, and OC expression in (C) MC3T3-E1 cells and (D) rBMSC.

In order to investigate the effect of BMP2 tethering on the scaffold osteoinductivity, hybrid scaffolds were characterized for osteoblast specific gene expressions. For this study, PLGA/nHA composite matrix was infused with self assembling peptide containing BMP2 and MC3T3-E1 cells/rBMSCs. The scaffold groups chosen for the investigation were the scaffolds with no BMP2, and scaffolds with BMP2 (un-tethered, tethered). All the groups were cultured in MM before analyzing them for gene expression at days, 7, and 14. Alkaline phosphatase (ALP), an early osteogenic marker, and osteocalcin (OC), a late osteogenic marker, were chosen for the analysis. FIG. 19 shows changes in mRNA expression levels of alkaline phosphatase and osteocalcin of pre-osteoblasts, and bone marrow cells cultured in hybrid scaffolds with tethered BMP2 or untethered BMP2. As shown in FIG. 19(*a*), no difference in ALP expression was observed on day 7 for all groups from MC3T3 cultures, but by day 14 tethered BMP2 group showed 1 and 0.5 fold increases over the control and un-tethered BMP2 groups, respectively. A similar trend was observed with rBMSC cultures (FIG. 19B), where the expression of ALP by day 14 was increased by 5 and 4 folds over the control and un-tethered BMP2 group, respectively (FIG. 19B). In the case of osteocalcin, as shown in (FIG. 19 C), the MC3T3—preosteoblasts cultures, showed no difference on day 7, but by day 14, the tethered BMP2 showed 5 and 2 fold increases respectively over control and un-tethered BMP2 groups. Osteocalcin expression was slightly different in rBMSC cultures (FIG. 19D), although BMP2 un-tethered showed 1 fold increase over BMP2 tethered group on day 7, by day 14, BMP2 tethered group had 2 fold more than BMP2 un-tethered group (FIG. 19D). Interestingly, both BMP2 tethered and BMP2 untethered showed 250 and 150 folds in OC expression than the control cultures on day 14 (FIG. 19D). These results shows that, although BMP2 can increase the expression of ALP and OC in these cultures, the tethering of BMP2 appears to be more effective, an indication of an osteoinductive hybrid scaffold.

Discussion

Scaffold-based bone regeneration efforts require biodegradable scaffolds with bone compatible mechanical properties. In a critically damaged bone, scaffolds provide physical support as well as surface for bone cell attachment and proliferation (Borden et al. 2002, Laurencin et al. 1999). The present study demonstrates the fabrication of a hybrid scaffold consisting of a mechanically strong nHA/PLGA three-dimensional scaffold infused with a peptide hydrogel conjugated with rhBMP2. PLGA materials have been extensively studied, and have been approved for certain clinical applications by the food and drug administration (FDA). Peptide hydrogels are an excellent cell encapsulating agents (Hosseinkhani, Hosseinkhani and Kobayashi 2006), and can form into ECM-like nano-fibrous structures. This study demonstrates encapsulation of BMSCs and pre-osteoblastsic cells in the hybrid system. Encapsulated cells showed robust growth and proliferation in the hybrid system as the components appear to work synergistically to promote growth and proliferation of the encapsulated cells. The presence of hydrogel nanofibers could provide ECM-like environment for the cells. This may be one of the reasons, why we observed superior proliferation in hybrid system than in PLGA scaffold alone (FIG. 15). This observation is consistent with previous reports showing that nanotopography present in RADA-16 gel promoted robust cell growth and proliferation of several cell types including bone forming cells (Meirelles et al. 2008, Oh et al. 2009). It was evident from our con-focal scanning microscope study that encapsulated cells within the spaces between microspheres 24 hours after cells were seeded on the scaffold. This is primarily due to the presence of nanogel which allows the cells to be retained within the scaffolds. Consequently, these cells proliferated and migrated towards the surfaces of the microspheres and eventually cellularizing the whole scaffold within 14 days. The hybrid scaffold design is such that initially hydrogel houses cells and provide ECM-like environment, but slowly as the hydrogel phase starts degrading the cells migrate towards the microsphere surfaces. Therefore, the hybrid scaffold combines the best qualities of the different starting materials, such that the PLGA provides the required mechanical strength, while the hydrogel would act as the cell encapsulating agent and also provides the nanotopography necessary for the cells to attach and proliferate.

The performance of many bone tissue engineered scaffolds is assessed not only by their ability to support cell growth and survival, but also whether they are able to deliver growth factors that can drive differentiation and maturation of implanted cells or cells attracted to the site of the defect. Thus, it is important to develop scaffolds that exhibit osteoconductivity, as well as osteoinductive capabilities. Here, this study demonstrates engineering a hybrid system with osteo-inductive ability. The present study demonstrates covalent binding of an osteoinductive growth factor, BMP2 to the SAP hydrogel. BMP2 is an osteogenic factor, which promotes proliferation and differentiation of bone marrow stromal cells towards the osteoblast lineage cells (Liu et al. 2009). Despite the wider use of BMP2 in many bone tissue regeneration studies, its short half-life remains a major limitation (Uludag et al. 1999b, Uludag et al. 1999a). The use of high doses of recombinant BMP2 and genetically engineered BMP2 producing cells are among some of the tissue engineering approaches that have been investigated as a way to increase BMP2 availability to the bone defect site (Laurencin et al. 2001). In this study, the approach taken was based on the biotinstreptavidin binding complexation. BMP2 tethering was intended to increase retention of BMP2 within the scaffold and possibly prolong its half-life. Streptavidin is a tetravalent protein with a high affinity to free biotin as well as biotin attached to a protein (Suter et al. 1988, Hendy et al. 1992) and has been used in growth factor conjugation studies. Moreover, successful biotinylation of BMP2 has been reported previously (Wiemann et al. 2002). Using a similar method, BMP2 biotin with a molar substitution ratio of 0.7-0.9 was achieved in this study. Furthermore, we confirmed the biological activity of BMP2-biotin using rBMSC and MC-3T3-E1 cells. The observation of comparable alkaline phosphatase activity and mineral deposition of biotin modified BMP2 and unmodified BMP2 groups is an indication that the BMP2 used in this study remained biologically active (FIG. 17). Although, it is expected that the BMP2 may lose some biological activity, the extent was not significant. This result is consistent with the findings in the study by Wiemann et al. (Wiemann et al. 2002).

Furthermore, tethering of BMP2 to the hybrid scaffold promoted osteogenic differentiation. This was evident by the increased expression of alkaline phosphatase by both the BMSCs and the MC3T3-E1 pre-osteoblasts cultured in hybrid scaffolds tethered with rhBMP2 (FIG. 19). A further evaluation of osteoblast differentiation marker osteocalcin demonstrated a significant fold increase confirming the osteoinductivity of the hybrid scaffold tethered with rhBMP2. It is interesting to note that delivering untethered BMP2 in the hybrid scaffolds demonstrated higher expression levels of alkaline phosphatase and osteocalcin than the control cultures. However, these osteoblast differentiation markers were lower in groups (BMP2 untethered and the control) when compared with the group that utilized tethered rhBMP2. A possible explanation may be that un-tethered BMP2 is released faster, whereas the tethered rhBMP2 is sequestered, and becomes slowly released as the hydrogel matrix degrades which is somewhat similar to the biological process whereby proteoglycans sequesters growth factors within the bone tissue, such that they are released during bone remodeling process to drive differentiation of osteoprogenitors (Bi et al. 2005). This is also supported by the BMP2 release kinetics data, whereby the factor release is slower in the tethered groups than in groups with free rhBMP2. Thus, tethering of rhBMP2 ensured its retention; consequently more rhBMP2 was available to the cells grown in the hybrid scaffold tethered with rhBMP2.

Conclusion

In this study, we have designed and fabricated a novel mechanically stable matrix loaded with hydrogel, a hybrid bone scaffold system. Additionally, the "polymer-hydrogel" hybrid scaffold system was successfully conjugated with recombinant human bone morphogenetic protein2 (rhBMP2) via biotin-streptavidin complexation strategy. By integrating hydrogel containing osteogenic cells and rhBMP2 with a polymer weight-bearing porous matrix, we have fabricated a hybrid scaffold system that display both the osteoinductivity and weight-bearing features possibly required for the repair and regeneration of large area/critical sized bone defects. Additionally, the novel "polymer-hydrogel" hybrid scaffold design allow for the amount of cell encapsulation required for bone tissue formation, so that the scaffold can be directly implanted in vivo without subjecting for in vitro culture. Designing such a self-reliant scaffold may be necessary for implementing in situ bone regeneration strategy for effectively treating bone defects.

References for Example 2

Amini, A., D. Adams, C. Laurencin & S. P. Nukavarapu. 2011. Development of Biodegradable Scaffolds with Adequate Porosity and Mechanical Strength for the Regeneration of Segmental Bone Defects (submitted to Tissue Engineering).

Andrassy, M., J. Igwe, F. Autschbach, C. Volz, A. Remppis, M. F. Neurath, E. Schleicher, P. M. Humpert, T. Wendt, B. Liliensiek, M. Morcos, S. Schiekofer, K. Thiele, J. Chen, R. Kientsch-Engel, A. M. Schmidt, W. Stremmel, D. M. Stern, H. A. Katus, P. P. Nawroth & A. Bierhaus (2006) Posttranslationally modified proteins as mediators of sustained intestinal inflammation. *Am J Pathol,* 169, 1223-37.

Aro, H. T. & A. J. Aho (1993) Clinical use of bone allografts. *Ann Med,* 25, 403-12.

Arrington, E. D., W. J. Smith, H. G. Chambers, A. L. Bucknell & N. A. Davino (1996) Complications of iliac crest bone graft harvesting. *Clin Orthop Relat Res,* 300-9.

Balasubramanian, N., P. Bai, G. Buchek, G. Korza & S. K. Weller (2010) Physical interaction between the herpes simplex virus type 1 exonuclease, UL12, and the DNA double-strand break-sensing MRN complex. *J Virol,* 84, 12504-14.

Bi, Y., C. Stuelten, T. Kilts, S. Wadhwa, R. Iozzo, P. Robey, X. Chen & M. Young (2005) Extracellular matrix proteoglycans control the fate of bone marrow stromal cells. *J Biol Chem,* 280, 30481-9.

Borden, M., M. Attawia & C. T. Laurencin (2002) The sintered microsphere matrix for bone tissue engineering: in vitro osteoconductivity studies. *J Biomed Mater Res,* 61, 421-9.

Brown, K. L. & R. L. Cruess (1982) Bone and cartilage transplantation in orthopaedic surgery. A review. *J Bone Joint Surg Am,* 64, 270-9.

Davis, M. E., P. C. Hsieh, T. Takahashi, Q. Song, S. Zhang, R. D. Kamm, A. J. Grodzinsky, P. Anversa & R. T. Lee (2006) Local myocardial insulin-like growth factor 1 (IGF-1) delivery with biotinylated peptide nanofibers improves cell therapy for myocardial infarction. *Proc Natl Acad Sci USA,* 103, 8155-60.

Delloye, C., O. Cornu, V. Druez & O. Barbier (2007) Bone allografts: What they can offer and what they cannot. *J Bone Joint Surg Br,* 89, 574-9.

Drury, J. L. & D. J. Mooney (2003) Hydrogels for tissue engineering: scaffold design variables and applications. *Biomaterials,* 24, 4337-51.

Geiger, M., R. H. Li & W. Friess (2003) Collagen sponges for bone regeneration with rhBMP-2. *Adv Drug Deliv Rev,* 55, 1613-29.

Guler, M. O., L. Hsu, S. Soukasene, D. A. Harrington, J. F. Hulvat & S. I. Stupp (2006) Presentation of RGDS epitopes on self-assembled nanofibers of branched peptide amphiphiles. *Biomacromolecules,* 7, 1855-63.

Hall, M. J. & M. F. Owings (2002) 2000 National Hospital Discharge Survey. *Adv Data,* 1-18.

Hendy, L. A., S. McGonigle, U. MacEvilly, R. Ryan & M. G. Harrington (1992) Streptavidin production by *Streptomyces avidinii* in a laboratory fermenter. *Biochem Soc Trans,* 20, 72S.

Hosseinkhani, H., M. Hosseinkhani & H. Kobayashi (2006) Proliferation and differentiation of mesenchymal stem cells using self-assembled peptide amphiphile nanofibers. *Biomed Mater,* 1, 8-15.

Husing, B., B. Buhrlen, and S. Gaisser. 2010. Human Tissue Engineered Products—Today's Markets and Future Prospects.

Igwe, J. C., Q. Gao, T. Kizivat, W. W. Kao & I. Kalajzic (2011) Keratocan is Expressed by Osteoblasts and Can Modulate Osteogenic Differentiation. *Connect Tissue Res.*

Jiang, T., S. P. Nukavarapu, M. Deng, E. Jabbarzadeh, M. D. Kofron, S. B. Doty, W. I. Abdel-Fattah & C. T. Laurencin (2010) Chitosan-poly(lactide-co-glycolide) microsphere-based scaffolds for bone tissue engineering: in vitro degradation and in vivo bone regeneration studies. *Acta Biomater,* 6, 3457-70.

Johnell, O. (1997) The socioeconomic burden of fractures: today and in the 21st century. *Am J Med,* 103, 20S-25S; discussion 25S-26S.

Kweon, H., M. K. Yoo, I. K. Park, T. H. Kim, H. C. Lee, H. S. Lee, J. S. Oh, T. Akaike & C. S. Cho (2003) A novel degradable polycaprolactone networks for tissue engineering. *Biomaterials,* 24, 801-8.

Laurencin, C., A. Ambrosio, M. Borden & J. J. Cooper (1999) Tissue engineering: orthopedic applications. *Annu Rev Biomed Eng,* 1, 19-46.

Laurencin, C., M. Attawia, L. Lu, M. Borden, H. Lu, W. Gorum & J. Lieberman (2001) Poly(lactide-co-glycolide)/hydroxyapatite delivery of BMP-2-producing cells: a regional gene therapy approach to bone regeneration. *Biomaterials,* 22, 1271-7.

Laurencin, C., Y. Khan & S. F. El-Amin (2006) Bone graft substitutes. *Expert Rev Med Devices,* 3, 49-57.

Lee, K., E. A. Silva & D. J. Mooney (2011) Growth factor delivery-based tissue engineering: general approaches and a review of recent developments. *J R Soc Interface,* 8, 153-70.

Liu, R., S. L. Ginn, M. Lek, K. N. North, I. E. Alexander, D. G. Little & A. Schindeler (2009) Myoblast sensitivity and fibroblast insensitivity to osteogenic conversion by BMP-2 correlates with the expression of Bmpr-1a. *BMC Musculoskelet Disord,* 10, 51.

Liu, X. & P. Ma (2004) Polymeric scaffolds for bone tissue engineering. *Ann Biomed Eng,* 32, 477-86.

Meirelles, L., A. Arvidsson, M. Andersson, P. Kjellin, T. Albrektsson & A. Wennerberg (2008) Nano hydroxyapatite structures influence early bone formation. *J Biomed Mater Res A,* 87, 299-307.

Mondrinos, M. J., R. Dembzynski, L. Lu, V. K. Byrapogu, D. M. Wootton, P. I. Lelkes & J. Zhou (2006) Porogen-based solid freeform fabrication of polycaprolactone-calcium phosphate scaffolds for tissue engineering. *Biomaterials,* 27, 4399-408.

Nakahara, H., H. Misawa, A. Yoshida, T. Hayashi, M. Tanaka, T. Furumatsu, N. Tanaka, N. Kobayashi & T. Ozaki (2010) Bone repair using a hybrid scaffold of self-assembling peptide PuraMatrix and polyetheretherketone cage in rats. *Cell Transplant,* 19, 791-7.

Nukavarapu, S. P., S. G. Kumbar, J. L. Brown, N. R. Krogman, A. L. Weikel, M. D. Hindenlang, L. S. Nair, H. R. Allcock & C. T. Laurencin (2008) Polyphosphazene/nanohydroxyapatite composite microsphere scaffolds for bone tissue engineering. *Biomacromolecules,* 9, 1818-25.

Nukavarapu S P, W. J., Elgendy H M, Lieberman J R, Laurencin C T. 2011. An Introduction to Biomaterials and their Applications. Taylor & Francis group.

Oh, S., K. Brammer, Y. Li, D. Teng, A. Engler, S. Chien & S. Jin (2009) Stem cell fate dictated solely by altered nanotube dimension. *Proc Natl Acad Sci USA,* 106, 2130-5.

Praemer, A. F., and D. P. Sylvia Rice. 1992. *Musculoskeletal Conditions in the <countryregion> United States</country-region>.* AAOS.

Sachse, A., A. Wagner, M. Keller, O. Wagner, W. D. Wetzel, F. Layher, R. A. Venbrocks, P. Hortschansky, M. Pietraszczyk, B. Wiederanders, H. J. Hempel, J. Bossert, J. Horn, K.

Schmuck & J. Mollenhauer (2005) Osteointegration of hydroxyapatite-titanium implants coated with nonglycosylated recombinant human bone morphogenetic protein-2 (BMP-2) in aged sheep. *Bone,* 37, 699-710.

Salgado, A. J., O. P. Coutinho & R. L. Reis (2004) Bone tissue engineering: state of the art and future trends. *Macromol Biosci,* 4, 743-65.

Sargeant, T. D., M. O. Guler, S. M. Oppenheimer, A. Mata, R. L. Satcher, D. C. Dunand & S. I. Stupp (2008) Hybrid bone implants: self-assembly of peptide amphiphile nanofibers within porous titanium. *Biomaterials,* 29, 161-71.

Suter, M., J. Cazin, J. E. Butler & D. M. Mock (1988) Isolation and characterization of highly purified streptavidin obtained in a two-step purification procedure from *Streptomyces avidinii* grown in a synthetic medium. *J Immunol Methods,* 113, 83-91.

Uludag, H., D. D'Augusta, R. Palmer, G. Timony & J. Wozney (1999a) Characterization of rhBMP-2 pharmacokinetics implanted with biomaterial carriers in the rat ectopic model. *J Biomed Mater Res,* 46, 193-202.

Uludag, H., J. Golden, R. Palmer & J. Wozney (1999b) Biotinated bone morphogenetic protein-2: In vivo and in vitro activity. *Biotechnol Bioeng,* 65, 668-72.

Wiemann, M., H. P. Jennissen, H. Rumpf, L. Winkler, M. Chatzinikolaidou, I. Schmitz & D. Bingmann (2002) A reporter-cell assay for the detection of BMP-2 immobilized on porous and nonporous materials. *J Biomed Mater Res,* 62, 119-27.

Zhang, S. (2002) Emerging biological materials through molecular self-assembly. *Biotechnol Adv,* 20, 321-39.

Example 3. Gradient Porous Scaffolds

Figure 21:
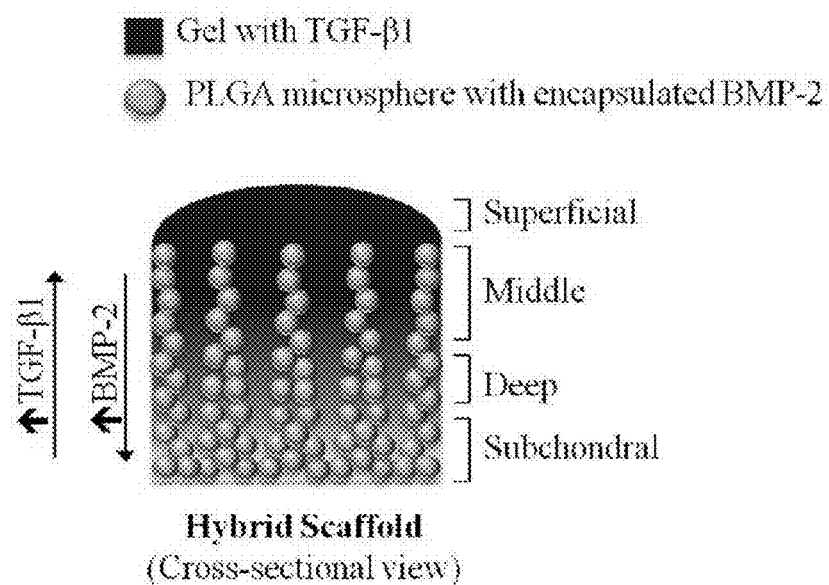
FIG. 21. Schematic showing a gradiently porous hybrid scaffold with required growth factor spatial distribution that can mimic and support zonal cartilage structure with the underlying subchondral bone FIG. 22. Image of a gradiently porous scaffold.

Articular cartilage is organized into zonal structure (deep, middle, and superficial zones). The deep zone is close to the bony end and mechanically stiff, while the middle and superficial zones consist of soft cartilage. There is gradual change in the amount of collagen and proteoglycans present from deep to superficial zones. To structurally mimic the articular cartilage, we have fabricated novel scaffolds with gradient porosity. The proposed hybrid scaffold with gradient porous structure mimics the native osteochondral structure physically while supporting chondroprogenitor cell survival. The bottom phase of the scaffold extends upwards with larger pore and increasing diameter from bottom to top that mimics the deep to middle zone. An exemplary representation of such a gradient porous scaffold is shown in FIG. 20. Optionally, a self-assembling peptide hydrogel can be used to fill the entire porous structure and constitute the superficial zone (see, for example, FIG. 21).

Poly (lactide-co-glycolide) (PLGA) 85:15 microspheres were prepared using an oil-in-water emulsion process. The resulting microspheres were then combined with 0, 5, 10, 20, and 40 weight percent NaCl porogen (200-300 μm). Gradient scaffolds were fabricated by sequentially adding the different polymer-porogen combinations, layer-by-layer, into the selected 15 mm height×5 mm diameter scaffold mold. For example, the above-described five layers gradient scaffold was prepared as follows:
1. Estimating the total scaffold weight;
2. Dividing the total weight with number of layers to estimate the weight required for each layer; 3. Placing the estimated amounts of polymer+porogen with porogen content 0, 5, 10, 20 and
40 wt % into a metallic mold;
4. Sintering at 101° C./1 hr; and
5. Soaking in water to dissolve NaCl porogen.

Figure 22:
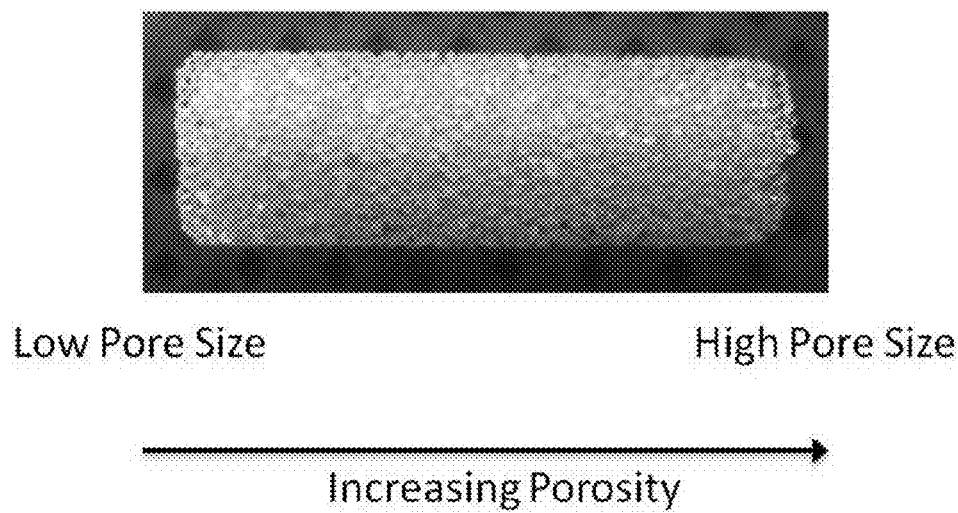

A representative image of the gradient porous scaffold is shown in FIG. 22. While the depicted scaffold contains only the five layers previously specified, we have also created scaffolds with five alternative contents (0, 5, 15, 30, and 50 weight percent porogen) as well as gradient scaffolds with linearly increasing pore volume provided by additional porogen layers (0, 4, 8, 12, 16, 20, 24, 28, 32, 36, and 40 weight percent porogen). Both the scaffold types (step gradient, linear gradient) were also fabricated into the 10 mm length×5 mm diameter cylinder. Some of these experiments also used porogen in the size range of 106-212 μm.

Figure 23:
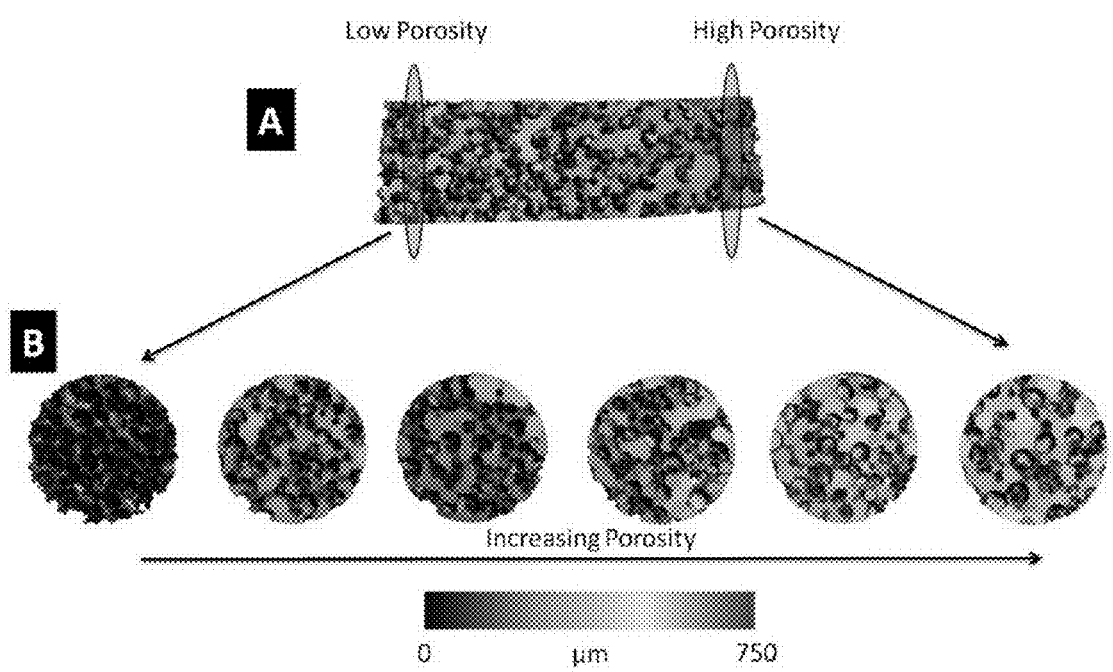
FIG. 23. Scaffold Pore Interconnectivity and Porosity via Micro-CT imaging and analysis of gradient scaffolds fabricated with 600-700 μm PLGA microspheres and 200-300 μm NaCl crystals. Accessible volume space images generated by imposing specific pore diameter parameters (scale 100-750 μm) on PLGA gradient scaffolds (15 mm height, 5 mm diameter from an (A) longitudinal view, and (B) cross-sectional view every 2 mm down the length of the scaffold. Analysis demonstrates an interconnectivity and accessible volume gradient in the porous scaffolds.
Figure 24:
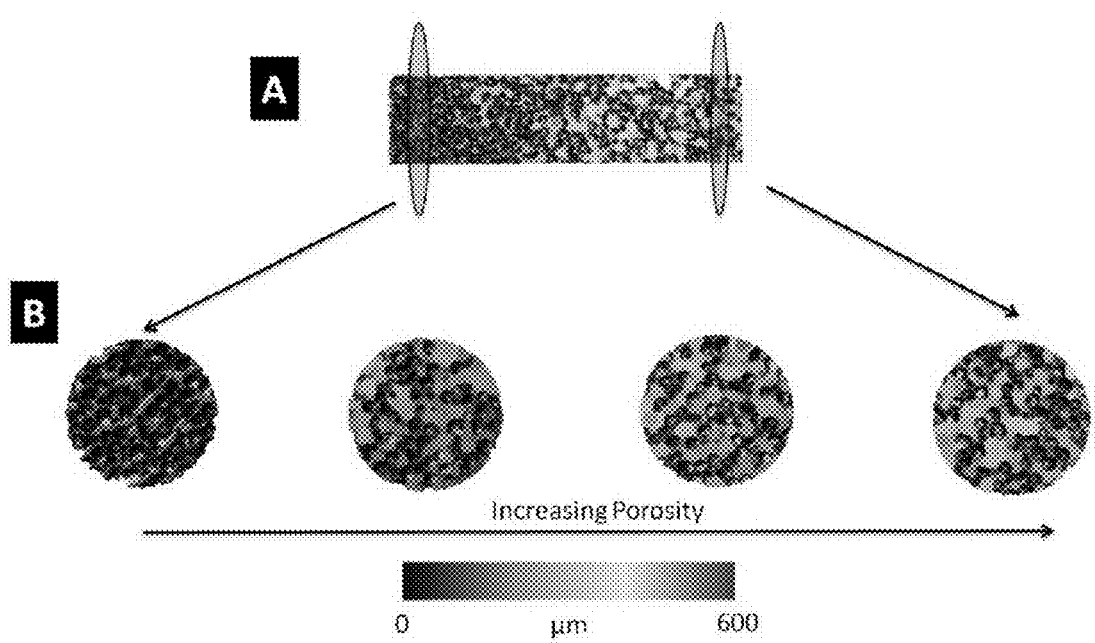
FIG. 24. Scaffold Pore Interconnectivity and Porosity via Micro-CT imaging and analysis of gradient scaffolds fabricated with 200-300 μm PLGA microspheres and 200-300 μm NaCl crystals. Accessible volume space images generated by imposing specific pore diameter parameters (scale 100-600 μm) on PLGA gradient scaffolds (15 mm height, 5 mm diameter from an (A) longitudinal view, and (B) cross-sectional view every 2 mm down the length of the scaffold. Analysis demonstrates an interconnectivity and accessible volume gradient in the porous scaffolds.

Initially, microspheres of two size ranges were used to fabricate two different gradient scaffolds. The first set was developed using 600-700 μm diameter spheres while the other was developed using a 200-300 μm sized range. In order to establish gradient structure of these scaffolds, Micro-Computed Tomography (μCT) analysis of pore interconnectivity and porosity was performed. Using this method, the accessible volume space was visualized, qualitatively, in both the scaffolds longitudinal and cross sections (See FIGS. 23-24). Based on these results, it was found that the size ranges between 200-700 μm could result in gradient matrix formation with pore sizes suitable for cell survival and tissue regeneration.

After testing the osteogenic and chondrogenic abilities of the polymer and polymer-hydrogel grafts respectively on disk scaffolds (2 mm×10 mm), the biomimetic structure was tested in vitro by embedding $5\times10^5$ human bone marrow derived stem cells (hBMSCs) into a self assembling peptide gel (PuraMatrix) (See Example 2) and infusing it into the pore spaces of the graft. Additionally, $1.3\times10^5$ hBMSCs were added to the cell culture media and agitated until they adhered to the scaffold. After 21 days of culture (in co-differentiation media) immunofluorescence staining was performed to determine the osteogenic and chondrogenic differentiation ability of the scaffold.

In vitro studies show that osteogenesis and chondrogenesis can be accomplished on the PLGA matrix in the absence of and with PuraMatrix hydrogel respectively, in which bone and cartilage scaffold layers in separate cultures and seeded with hMSCs displayed (A) Collagen I, (B) Runx2, and (C) Tubulin as well as (D) Collagen II, (E) Sox9, and (F) Tubulin expression (data not shown). After combining both osteogenic and chondrogenic media in a 50:50 ratio to create a co-differentiation media, it was found that the hBMSCs seeded in the gradient scaffolds are capable of osteochondral differentiation as seen by the cells simultaneous display of osteogenic matrix marker, Collagen I, and chondrogenic matrix marker, Collagen II (data not shown).

Conclusions

Our studies, for the first time, have led to the development of a gradient matrix system that promotes hierarchically structured osteochondral tissue regeneration. Bone and cartilage phases of the scaffolds seeded with human BMSCs independently confirmed their potential to support osteogenic and chondrogenic differentiation, respectively. This study also developed a co-differentiation media for OC graft culture in vitro.

We claim:

1. A gradient porous scaffold, comprising a plurality of biodegradable microspheres that are joined to form a scaffold, wherein the scaffold comprises a continuous porosity gradient along the length of the scaffold, wherein a first end of the scaffold has a porosity of between about 10% to about 40%, and a second end of the scaffold has a porosity of between about 65% to about 75%, wherein the gradient porous scaffold is made by a process comprising:
   (a) mixing a plurality of microspheres with porogen in a desired ratio to produce a mixture, wherein the mixing comprises,
      (i) mixing the plurality of microspheres with different ratios of porogen to produce a plurality of mixes;
      (ii) combining the plurality of mixes to produce the mixture, such that a ratio of the porogen increases continuously along a length of the mixture;
   (b) sintering the mixture for a suitable time and under suitable conditions to bond adjacent microspheres, producing a sintered mixture; and
   (c) leaching porogen from the sintered mixture to produce a gradient porous scaffold having the continuous gradient along the length of the scaffold.

2. The gradient porous scaffold of claim 1, wherein the microspheres are between about 200 μm in diameter and about 700 μm in diameter.

3. The gradient porous scaffold of claim 1, wherein the biodegradable microspheres comprise poly(lactide-co-glycolide acid) (PLGA).

4. The gradient porous scaffold of claim 1, further comprising a gel within the scaffold.

5. The gradient porous scaffold of claim 4, wherein the gel comprises a hydrogel.

6. The gradient porous scaffold of claim 1, further comprising cells and/or growth factors associated with the scaffold.

7. The gradient porous scaffold of claim 1, wherein the scaffold has a percent accessible pore volume of between about 30% to about 60%.

8. The gradient porous scaffold of claim 7, wherein the scaffold has an average pore size of greater than 300 μM in diameter.

9. The gradient porous scaffold of claim 8, wherein the scaffold has an average pore size of between about 300 μm in diameter and about 500 μm in diameter.

10. The gradient porous scaffold of claim 1, wherein the first end is present within a first region of the scaffold, wherein the first region comprises about 40% to about 70% of the length of the scaffold.

11. The gradient porous scaffold of claim 1, wherein the second end is present within a second region of the scaffold, wherein the second region comprises about 5% to about 20% of the length of the scaffold.

12. The gradient porous scaffold of claim 10, wherein the second end is present within a second region of the scaffold, wherein the second region comprises about 5% to about 20% of the length of the scaffold.

13. A continuous gradient porous scaffold, wherein the scaffold comprises at least 4 zones, wherein
   (a) a first zone includes a first end of the scaffold and includes a porosity of about 10% at a first end of the first zone and a porosity of about 40% at a second end of the first zone;
   (b) a second zone contiguous to the first zone has a porosity of between about 45% at a first end of the second zone adjacent to the first zone and a porosity of about 55% at a second end of the second zone;
   (c) third zone contiguous to the second zone has a porosity of between about 55% at a first end of the third zone adjacent to the second end of the second zone and a porosity of about 65% at a second end of the third zone; and
   (d) a fourth zone contiguous to the third zone and including the second end of the scaffold has a porosity of between about 65% at a first end of the fourth zone adjacent to the third zone and a porosity of about 75% at a second end of the fourth zone;
   wherein the gradient porous scaffold further comprises a hydrogel within the scaffold, wherein an increased amount of the hydrogel is present in the fourth zone compared to the second zone.

14. The gradient porous scaffold of claim 13, wherein the first zone comprises about 40% to about 70% of the length of the scaffold.

15. The gradient porous scaffold of claim 14, wherein the second zone comprises about 5% to about 20% of the length of the scaffold.

16. The gradient porous scaffold of claim 15, wherein the third zone comprises about 5% to about 20% of the length of the scaffold.

17. The gradient porous scaffold of claim 16, wherein the fourth zone comprises about 5% to about 20% of the length of the scaffold.

18. The gradient porous scaffold of claim 5, where in the hydrogel is biodegradable.

* * * * *